United States Patent [19]
Mizutani et al.

[11] Patent Number: 5,312,913
[45] Date of Patent: May 17, 1994

[54] ELECTRICALLY CONDUCTIVE COMPLEX

[75] Inventors: Makoto Mizutani; Kazushige Kawabata; Keiji Tanaka, all of Sodegaura, Japan

[73] Assignee: Idemitsu Kosan Co., Ltd., Tokyo, Japan

[21] Appl. No.: 953,746

[22] Filed: Sep. 29, 1992

Related U.S. Application Data

[62] Division of Ser. No. 690,973, filed as PCT/JP90/01518, Nov. 21, 1990, Pat. No. 5,175,280.

[30] Foreign Application Priority Data

Nov. 21, 1989 [JP] Japan .................... 1-300874
Jun. 15, 1990 [JP] Japan .................... 2-157310
Oct. 5, 1990 [JP] Japan .................... 2-266612

[51] Int. Cl.$^5$ ............... C07D 339/06; C07D 343/00; C07D 345/00; C07D 421/10
[52] U.S. Cl. ............................. 540/1; 549/3; 549/30; 549/32; 549/39
[58] Field of Search .................. 540/1; 549/39, 32, 3, 549/30

[56] References Cited

U.S. PATENT DOCUMENTS 4,249,013 2/1981 Haddon et al. .
4,691,028 9/1987 Inokuchi et al. .

FOREIGN PATENT DOCUMENTS 58-62171 4/1983 Japan .

Primary Examiner—Robert Gerstl
Attorney, Agent, or Firm—Frishauf, Holtz, Goodman & Woodward

[57] ABSTRACT

An electrically conductive complex obtained by reacting a thia-and/or selenafulvalenyl group-containing compound as an electron donor with an electron acceptor, and having an electron donar/electron acceptor molar ratio of 1/0.1 to 1/10, the thia-and/or selenafulvalenyl group-containing compound having the formula (I),

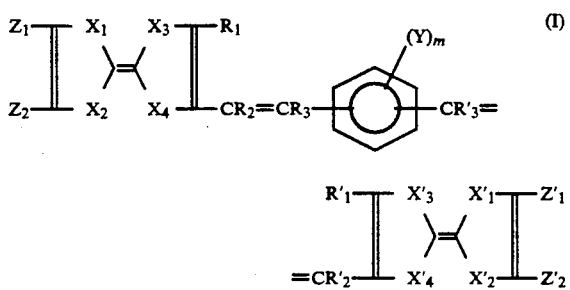

wherein each of $X_1$, $X_2$, $X_3$, $X_4$, $X'_1$, $X'_2$, $X'_3$ and $X'_4$ is independently S or Se, Y is an electron donating or electron accepting group having a size which is not so large as to prevent molecular overlapping, m is an integer of 0 to 4, each of $Z_1$, $Z_2$, $Z'_1$ and $Z'_2$ is independently a hydrogen atom, $C_nH_{2n+1}$ in which n is an integer of 1 to 5, or alternatively, a combination of $Z_1$ with $Z_2$ or $Z'_2$ and is $C_nH_{2n}$ in which n is an integer of 1 to 5, or $X(C_nH_{2n})_{n'}X$ in which X is S or Se and n' is an integer of 1 to 3, and each of $R_1$, $R_2$, $R_3$, $R'_1$, $R'_2$ and $R'_3$ is independently a hydrogen atom or $C_nH_{2n+1}$ in which n is an integer of 1 to 5.

12 Claims, 17 Drawing Sheets

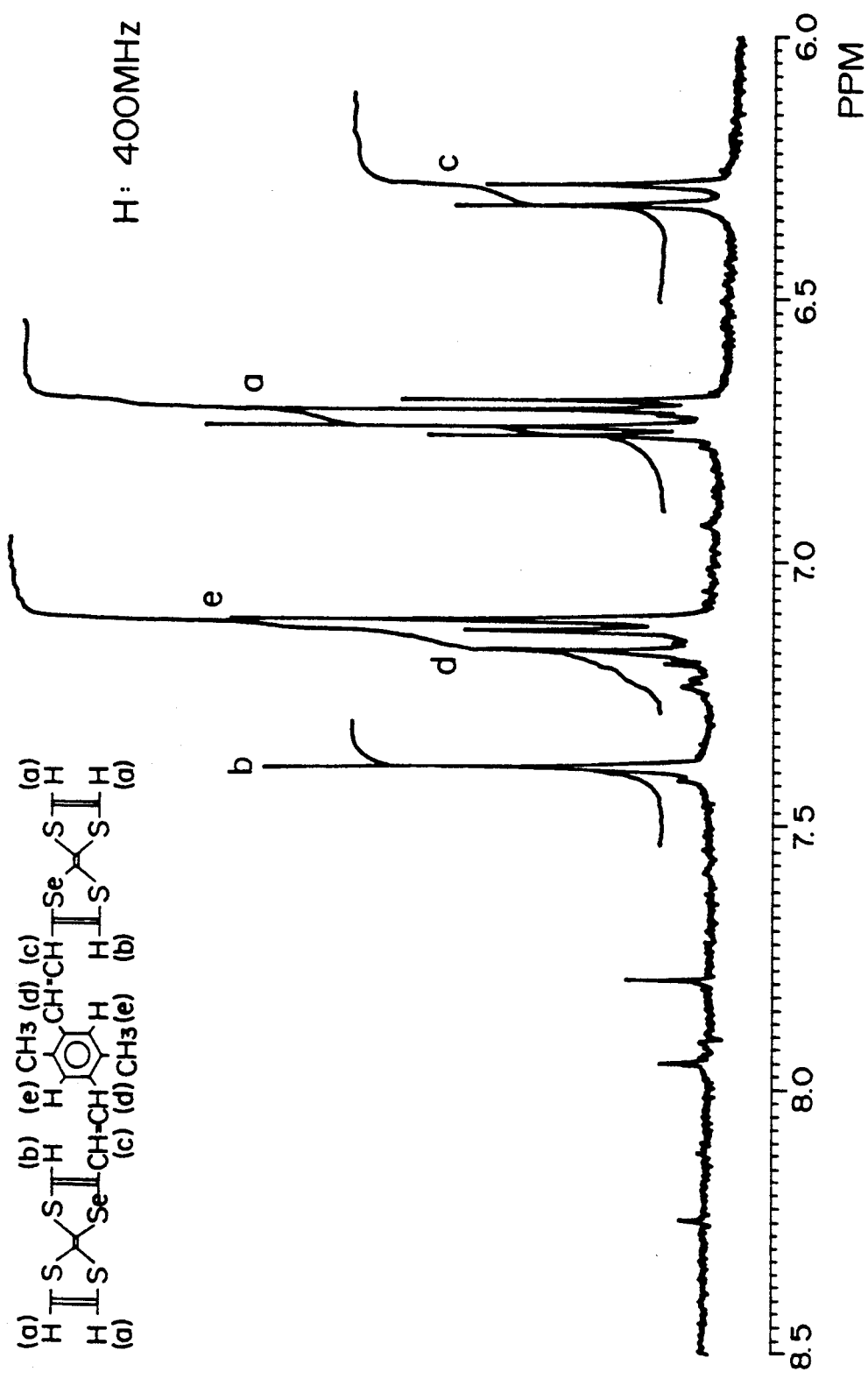

ELECTRICALLY CONDUCTIVE COMPLEX

This is a division of application Ser. No. 07/690,973, filed Jun. 17, 1991, which is a U.S. designated application of PCT/JP 90/0518, filed Nov. 21, 1990, which is now U.S. Pat. No. 5,175,280, issued Dec. 29, 1992.

TECHNICAL FIELD

This invention relates to a novel thia- and/or selenafulvalenyl group-containing compound and an electrically conductive complex containing this novel compound as an electron donor, and more specifically to a novel thia- and/or selenafulvalenyl group-containing compound having (i) the advantages of electron donating nature and capability of giving an electrically conductive complex when only mixed with an electron acceptor and (ii) the advantages of excellent thermal stability, etc., and an electrically conductive complex containing this novel compound as an electron donor.

TECHNICAL BACKGROUND

Although organic compounds have been generally considered to be insulating materials, researches are being energetically conducted in order to discover an organic compound having electrical conductivity. As an organic electrically conductive compound, there is known a charge-transfer complex in which an electron donor and an electron acceptor are bonded to each other due to charge transfer between these two members.

It is already known that complexes obtained by reacting a variety of electron acceptors with compounds having a thiafulvalene skeleton such as tetrathiafulvalene (TTF), tetramethyltetrathiafulvalene (TMTTF), bisethylenedithiotetrathiafulvalene (BEDTTTF), etc., exhibit relatively good electrical conductivity [a Japanese periodical "Kagaku Sosetsu", Vol. 42, page 59 (1983)].

However, among the above electron-donating compounds having a thiafulvalene skeleton, TTF has the following defect:.It is inferior in thermal stability due to its low melting point of 115 to 119° C. and cannot be applied to a part exposed to a high temperature, and the area for its use is hence limited. TMTTF and BEDTTTF have excellent thermal stability over TTF, but have the following defect: these compounds have no sufficient electron donating nature, and cannot form a complex when only directly mixed with a generally used electron acceptor, and it is required to employ a complicated method such as an electrolytic crystallization method, or the like, in order to form a complex.

As described above, no organic compound has been found so far which has good electron donating nature, the capability of directly forming a complex with an electron acceptor and excellent thermal stability.

Therefore, it is a first object of this invention to provide a novel organic compound having good electron donating nature, the capability of directly forming a complex with an electron acceptor and excellent thermal stability.

Further, it is a second object of this invention to provide an electrically conductive complex containing, as an electron donor, a novel organic compound having good electron donating nature, the capability of directly forming a complex with an electron acceptor and excellent thermal stability.

DISCLOSURE OF THE INVENTION

The present inventors have made a diligent study to achieve the above objects and as a result, found the following. (1) The organic compound of the general formula (I), in which each of the two ends is terminated with a specific thia- and/or selenafulvalenyl group and each group is bonded with a specific aromatic divinyl group, has good electron donating nature, the capability of directly forming a complex with an electron acceptor and excellent thermal stability. And, (2) a complex containing the organic compound of the general formula (I) as an electron donor, which is obtained by reacting this electron donor with an electron acceptor and has a specific molar ratio between the electron donor and the electron acceptor, has electrical conductivity. This invention has been completed on these findings.

That is, this invention has its gist in a thia- and/or selenafulvalenyl group-containing compound of the general formula (I),

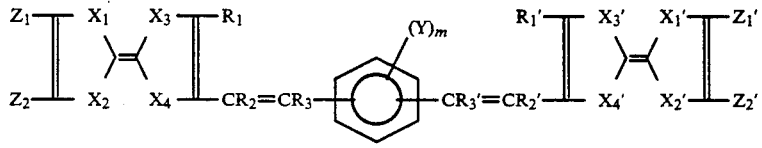

wherein:
each of $X_1$, $X_2$, $X_3$, $X_4$, $X'_1$, $X'_2$, $X'_3$ and $X'_4$ is independently S or Se,
Y is an electron donating or electron accepting substituent having a size which is not so large as to prevent molecular overlapping,
m is an integer of 0 to 4,
each of $Z_1$, $Z_2$, $Z'_1$ and $Z'_2$ is independently a hydrogen atom, $C_nH_{2n+1}$ in which n is an integer of 1 to 5, or $XC_nH_{2n+1}$ in which X is S or Se and n is an integer of 1 to 5, or alternatively, a combination of $Z_1$ with $Z_2$ and that of $Z'_1$ with $Z'_2$ are $C_nH_{2n}$ in which n is an integer of 1 to 5, or $X(C_nH_{2n})_{n'}X$ in which X is S or Se and n' is an integer of 1 to 3, and
each of $R_1$, $R_2$, $R_3$, $R'_1$, $R'_2$ and $R'_3$ is independently a hydrogen atom or $C_nH_{2n+1}$ in which n is an integer of 1 to 5.

This invention also has its gist in an electrically conductive complex containing the thia- and/or selenafulvalenyl group-containing compound of the general formula (I) as an electron donor, which is obtained by reacting this electron donor with an electron acceptor and has an electron donor/electron acceptor molar ratio of 1/0.1 to 1/10.

BRIEF DESCRIPTION OF THE DRAWINGS

FIG. 17 is an $^1$H-NMR analysis chart of a compound of this invention, obtained in Example 21.

PREFERRED EMBODIMENTS OF THE PRESENT INVENTION

Figure 1:
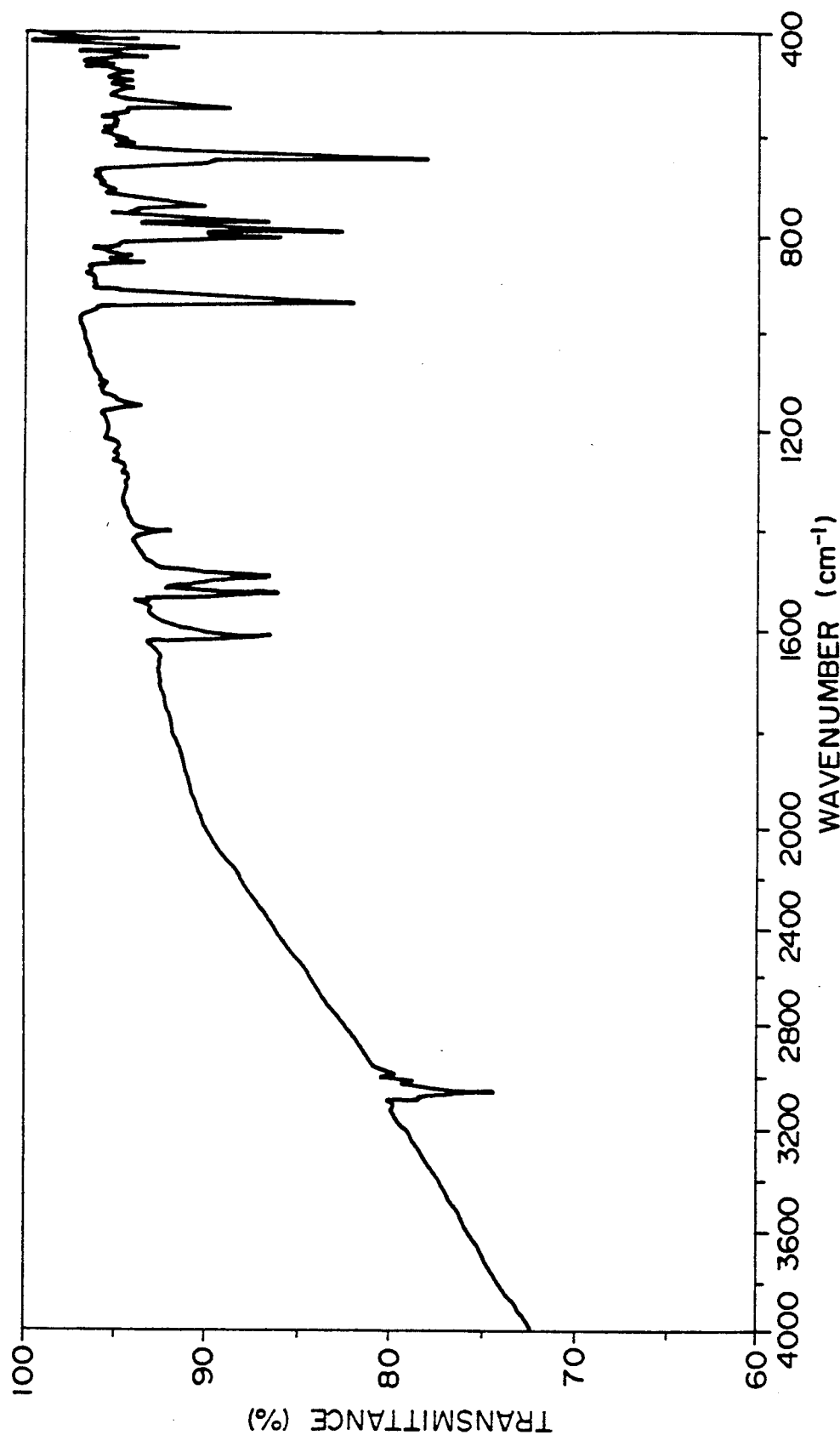
FIG. 1 is an IR analysis chart of a compound of this invention, obtained in Example 1.

As is clear in the above general formula (I), the novel thia- and/or selenafulvalenyl group-containing compound of this invention has thia- and/or selenafulvalenyl groups of the general formulae, one in one terminal and the other in the other terminal.

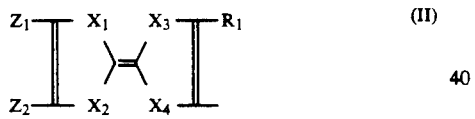

(II)

and

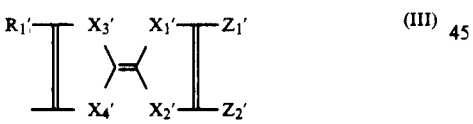

(III)

In the general formulae (II) and (III), each of $X_1$, $X_2$, $X_3$, $X_4$, $X'_1$, $X'_2$, $X'_3$ and $X'_4$ is independently S or Se. Therefore, specific examples of the general formulae (II) and (III) are as follows, although the general formulae shall not be limited thereto.

Specific examples of the general formula (II) are as follows:

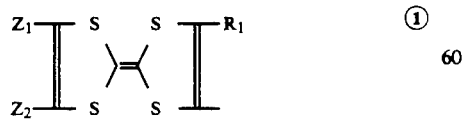

(1)

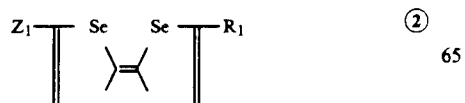

(2)

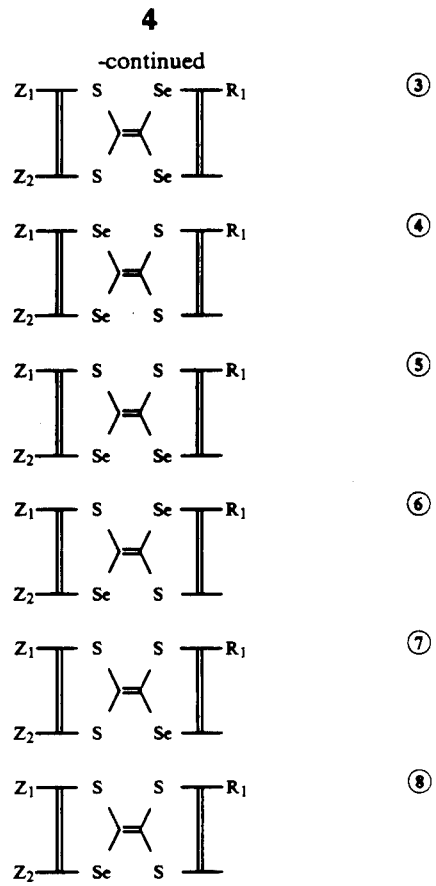

Specific examples of the general formula (III) are as follows:

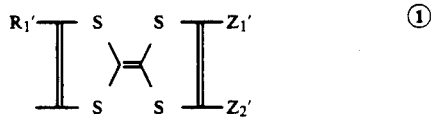

(1)

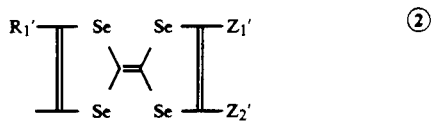

(2)

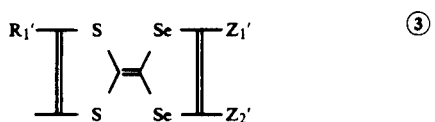

(3)

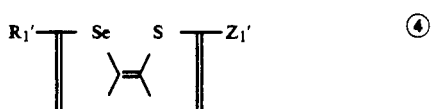

(4)

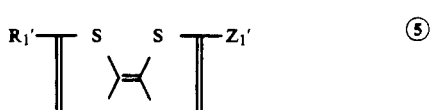

(5)

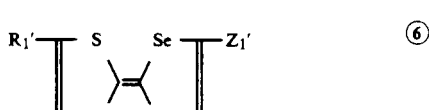

(6)

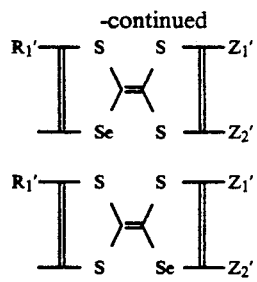

In the above example groups of the general formulae (II) and (III), each of $Z_1$, $Z_2$, $Z'_1$ and $Z'_2$ is independently a hydrogen atom, a lower alkyl group of the formula of $C_nH_{2n+1}$ in which n is an integer of 1 to 5, or a thio- or seleno-lower alkoxy group of the formula of $XC_nH_{2n+1}$ in which X is S or Se and n is an integer of 1 to 5. The lower alkyl group of the formula of $C_nH_{2n+1}$ is selected from methyl, ethyl, n-propyl, iso-propyl, n-butyl, iso-butyl and tert-butyl groups, and the like. The thio- or seleno-lower alkoxy group of the formula of $XC_nH_{2n+1}$ is selected from thiomethoxy, selenomethoxy, thioethoxy, selenoethoxy, thio-n-propoxy, seleno-n-propoxy, thio-iso-propoxy, seleno-iso-propoxy, thio-n-butoxy, seleno-n-butoxy, thio-iso-butoxy, seleno-iso-butoxy, thio-tert-butoxy and seleno-tert-butoxy groups, and the like.

In the above example groups of the formulae (II) and (III), $Z_1$ and $Z_2$ may be bonded to each other, and $Z'_1$ and $Z'_2$ may be bonded to each other, to form an alkylene of the formula of $C_nH_{2n}$ in which n is an integer of 1 to 5, or an alkylene group having sulfur and/or selenium atoms in the terminals, represented by the formula of $X(CH_2)_{n'}X$ in which X is S or Se and n' is an integer of 1 to 5, such as a dithioalkylene or a diselenoalkylene group. Typical examples of the alkylene group of the formula $C_nH_{2n}$ are methylene, ethylene, propylene and butylene groups, and typical examples of the alkylene group having sulfur and/or selenium atoms in the terminals, represented by the formula of $X(CH_2)_{n'}X$, are S—$CH_2$—S, Se—$CH_2$—Se, S—$(CH_2)_2$—S, Se—$(CH_2)_2$—Se, etc.

In the above example groups of the formulae (II) and (III), each of $R_1$ and $R'_1$ is independently a hydrogen atom or $C_nH_{2n+1}$ in which n is an integer of 1 to 5. A lower alkyl group of $C_nH_{2n+1}$ is selected from methyl, ethyl, n-propyl, iso-propyl, n-butyl, iso-butyl and tert-butyl groups, and the like.

The compound of the general formula (I), provided by this invention, is a compound having the thia@and-/or selenafulvalenyl groups of the above general formulae (II) and (III), one in its one terminal and the other in the other terminal, and being formed by bonding these groups with an aromatic divinyl group of the general formula (IV).

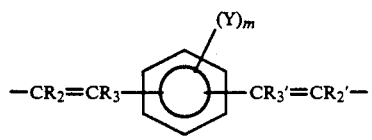

In the general formula (IV), Y is an electron donating or electron accepting group having a size which is not so large as to prevent molecular overlapping. Typical examples of the electron donating group are lower alkyl groups having 1 to 5 carbon atoms such as methyl, ethyl, n-propyl, iso-propyl, n-butyl, iso-butyl, tert-butyl and other groups, lower alkoxy groups having 1 to 5 carbon atoms such as methoxy, ethoxy and other groups, thio-lower alkoxy groups having 1 to 5 carbon atoms such as thiomethoxy, thioethoxy and other groups, an amino group, a hydroxyl group, etc. Typical examples of the electron accepting group are halogen atoms such as chlorine, bromine, iodine, etc., a cyano group, a nitro group, etc.

In the formula (IV), each of $R_2$, $R_3$, $R'_2$ and $R'_3$ is independently a hydrogen atom or $C_nH_{2n+1}$ in which n is an integer of 1 to 5. Typical examples of a lower alkyl group of the formula of $C_nH_{2n+1}$ are methyl, ethyl, n-propyl, iso-propyl, n-butyl, iso-butyl, tert-butyl and other groups.

The compound of the general formula (I), provided by this invention, can be produced, e.g. by a known Wittig reaction. One preferred process for the production thereof is as follows. In an ether-containing or alcohol-containing solvent, 1 mol of a formylthia and-/or selenafulvalene-based compound such as formyltetrathiafulvalene, formyltetraselenafulvalene, or the like and 0.5 mol of xylylenebis(triphenylphosphonium chloride) are reacted with each other in the presence of 1 mol of a suitable base such as sodium ethoxide, n-butyllithium, t-butoxypotassium, or the like at a room temperature for several minutes to about 10 hours, whereby a desired compound can be obtained. When the reaction time is shorter than the above range, the yield is low. Even-when the reaction is continued longer than the above range, the yield arrives at its peak, and no further improvement in the yield can be expected. In this reaction, the above xylylenebis(triphenylphosphonium chloride) may be replaced with xylylenebis(triphenylphosphonium chloride) or xylylenebis(triphenylphosphonium bromide) having a substituent of $(Y)_m$ on the benzene ring, whereby a compound of the general formula (I) having $(Y)_m$ as a substituent can be obtained.

Typical examples of the compound of the general formula (I) are as follows.

Compound (Ia)
1,4-bis[2-(tetrathiafulvalen-2-yl)vinyl]benzene
Compound (Ib)
1,4-bis[2-(tetrathiafulvalen-2-yl)vinyl]-2,5-dimethylbenzene
Compound (Ic)
1,4-bis[2-(tetraselenafulvalen-2-yl)vinyl]-2,5-dimethylbenzene
Compound (Id)
1,4-bis[2-(3,6,7-trimethyltetraselenafulvalen-2-yl)vinyl]benzene
Compound (Ie)
1,4-bis[2-(6,7-ethylenedithiotetrathiafulvalen-2-yl)vinyl]-2.5-dimethylbenzene
Compound (If)
1,4-bis[2-(6,7-dimethylthiotetrathiafulvalen-2-yl)vinyl]-2,5-dimethylbenzene
Compound (Ig)
1,4-bis[2-(tetrathiafulvalen-2-yl)vinyl]-2-methoxybenzene
Compound (Ih)
1,4-bis[2-(tetrathiafulvalen-2-yl)vinyl]-2-chlorobenzene
Compound (Ii)
1,4-bis[2-(3,6,7-trimethyltetrathiafulvalen-2-yl)vinyl]benzene
Compound (Ij)

1-[2-(tetrathiafulvalen-2-yl)vinyl]-4-[2-(6,7-methylenedithiotetrathiafulvalen-2-yl]vinyl]-2,5-dimethylbenzene
Compound (Ik)

1-[2-(tetrathiafulvalen-2-yl)vinyl]-4-[2-(6,7-ethylenedithiotetrathiafulvalen-2-yl]vinyl]-2,5-dimethylbenzene
Compound (Il)

1-[2-(tetrathiafulvalen-2-yl)vinyl]-4-[2-(tetraselenafulvalen-2-yl]vinyl]-2,5-dimethylbenzene
Compound (Im)

1,4-bis[2-(tetrathiafulvalen-2-yl)vinyl]-2,5-dimethoxybenzene
Compound (In)

1,4-bis[2-(tetrathiafulvalen-2-yl)vinyl]-2,5-dichlorobenzene
Compound (Io)

1,4-bis[2-(tetrathiafulvalen-2-yl)vinyl]-2,3,5,6-tetramethylbenzene
Compound (Ip)

1,4-bis[2-(tetrathiafulvalen-2-yl)vinyl]-2-methyl benzene
Compound (Iq)

1,4-bis[2-(tetrathiafulvalen-2-yl)vinyl]-2,5-dihydroxybenzene
Compound (Ir)

1,4-bis[2-(1,4-dithia-5,8-diselenafulvalen-2-yl)vinyl]-2,5-dimethylbenzene
Compound (Is)

1,4-bis[2-(1,4-diselena-5,8-dithiafulvalen-2-yl)vinyl]-2,5-dimethylbenzene
Compound (It)

1,4-bis[2-(tetraselenafulvalen-2-yl)vinyl]-2,5-dichlorobenzene
Compound (Iu)

1,4-bis[2-(4,5,8-trithia-1-selenafulvalen-2-yl)vinyl]-2,5-dimethylbenzene

The compound of the general formula (I), provided by this invention, has electron donating nature and can form an electrically conductive complex not only by a general electrochemical method but also by only directly mixing it with an electron acceptor. The electron acceptor used for forming an electrically conductive complex may be any of organic and inorganic electron acceptors. The organic electron acceptor can be selected, for example, from 7,7,8,8-tetracyanoquinodimethane, 2-methyl-7,7,8,8-tetracyanoquinodimethane, 2,5-dimethyl-7,7,8,8-tetracyanoquinodimethane, 2,5-diethyl-7,7,8,8-tetracyanoquinodimethane, 2-methoxy-7,7,8,8-tetracyanoquinodimethane, 2,5-dimethoxy-7,7,8,8-tetracyanoquinodimethane, 2-methoxy-5-ethoxy-7,7,8,8-tetracyanoquinodimethane, 2-methoxydihydrodioxabenzo-7,7,8,8-tetracyanoquinodimethane, 2-chloro-7,7,8,8-tetracyanoquinodimethane, 2-bromo-7,7,8,8-tetracyanoquinodimethane, 2,5-dibromo-7,7,8,8-tetracyanoquinodimethane, 2,5-diiodo-7,7,8,8-tetracyanoquinodimethane, 2-chloro-5-methyl-7,7,8,8-tetracyanoquinodimethane, 2-bromo-5-methyl-7,7,8,8-tetracyanoquinodimethane, 2-iodo-5-methyl-7,7,8,8-tetracyanoquinodimethane, 11,11,12,12-tetracyano-2,6-naphthoquinodimethane, 1,1,2,3,4,4-hexacyanobutadiene, sodium-13,13,14,14-tetracyanodiphenoxydimethane, tetracyanoethylene, o-benzoquinone, p-benzoquinone, 2,6-naphthoquinone, diphenoquinone, tetracyanodiquinone, p-fluoranil, tetrachlorodiphenoquinone, etc. The inorganic electron acceptor is selected, for example, from halogen elements such as iodine, bromine, chlorine, etc., trihalide anions such as $I_3$, $I_2Br$, $IBr_2$, $Br_3$, $Cl_3$, etc., SCN, $Cu(SCN)_2$, $AuI_2$, $AuBr_2$, $AuCl_2$, etc. and electron accepting molecules such as $ClO_4$, $PF_6$, $BF_4$, etc.

In this charge-transfer complex, the molar ratio (D/A) of the electron donor (the compound of the general formula (I) provided by this invention) to the electron acceptor is 1/0.1 to 1/10. The reason therefor is as follows. When the D/A exceeds 1/0.1, the electrical conductivity is decreased, and when the D/A is less than 1/10, a decrease in the electrical conductivity is similarly observed. The so-obtained complex has electrical conductivity and can be used as an organic electrically conductive material.

The compound of the general formula (I), provided by this invention, has excellent thermal stability over existing tetrathiafulvalene (TTF), and therefore can expand the fields and areas where this compound and a complex obtained by a reaction between this compound and an electron acceptor are used. For example, a complex containing the compound of the general formula (I), provided by this invention, as an electron donor can be applied to an automobile-use printed circuit board exposed to a high temperature.

This invention will be explained further in detail hereinafter.

Preparation of compound of general formula (I) provided by this invention .

EXAMPLE 1

Preparation of 1,4-bis[2-(tetrathiafulvalen-2-yl)vinyl]benzene [Compound (Ia)]

2.18 Grams (3.1 mmol) of p-xylylenebis(triphenylphosphonium chloride) was suspended in 15 ml of THF, and 5 ml of a hexane solution of n-butyllithium (concentration 14% by weight) was added to the resultant suspension under argon gas current. Thereafter, a solution containing 1.43 g (6.16 mmol) of 2-formyltetrathiafulvalene and 10 ml of THF was added dropwise, and the resultant mixture was allowed to react at room temperature for 6 hours with stirring. Then, 50 ml of methanol was added to terminate the reaction, and the reaction mixture was filtered to obtain a reaction product. The reaction product was consecutively washed with methanol, washed with water, washed with methanol, recrystallized from dimethylformamide (to be referred to as DMF hereinafter), and then dried to give 0.60 g of a reddish brown solid (yield 36%). The reddish brown solid obtained in this Example 1, i.e. Compound (Ia), had a thermal decomposition temperature, Td, of 225° C. (The thermal decomposition temperature was defined as a temperature at which the weight decreased by 5% by weight according to TG (thermogravimetric analysis)), and was found to be excellent in thermal stability. Elemental analysis thereof showed the following.

|  | C | H | S |
| --- | --- | --- | --- |
| Calculated (%) | 49.4 | 2.6 | 47.9 |
| Found (%) | 49.5 | 2.7 | 47.8 |

Figure 2:
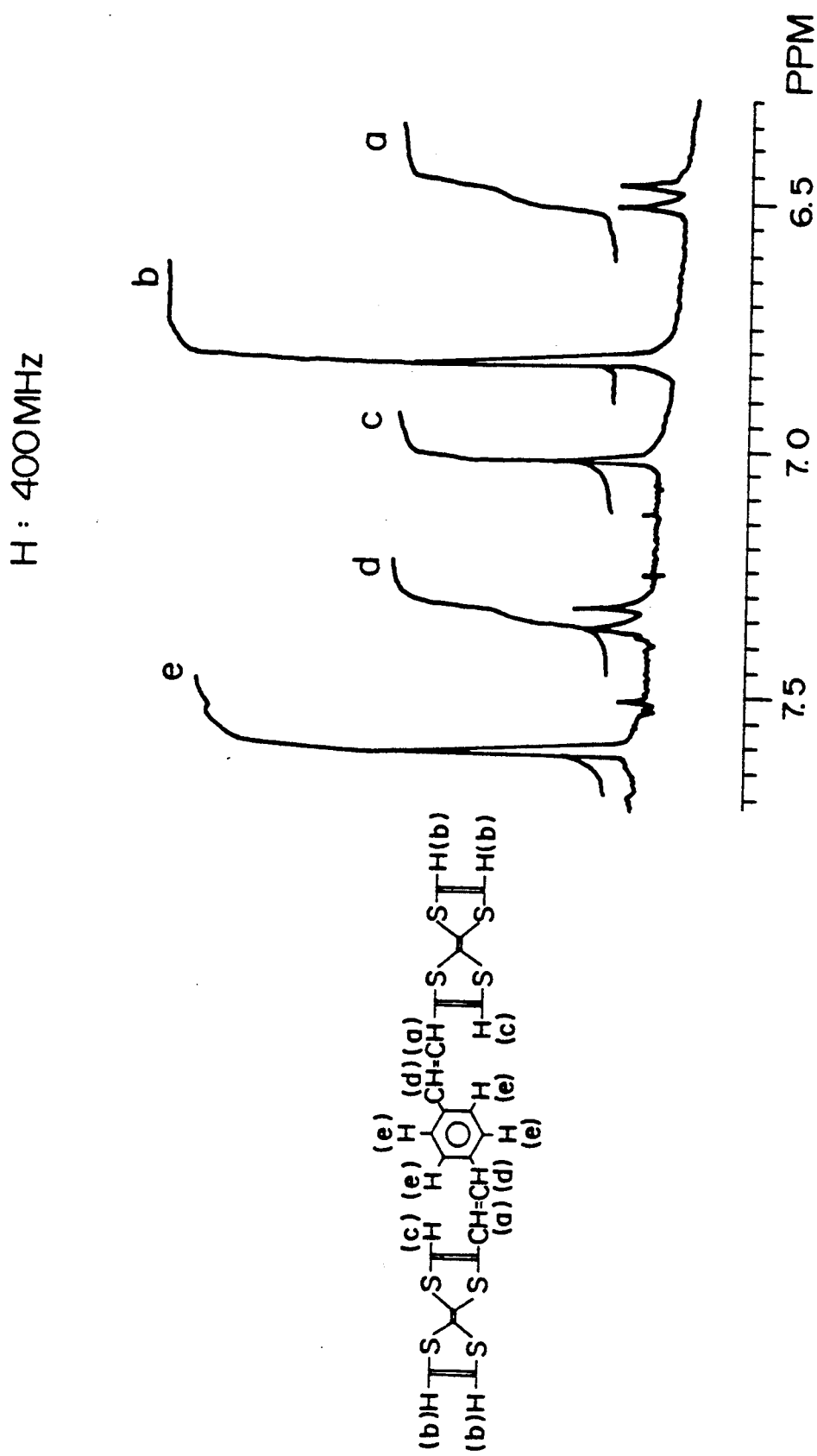
FIG. 2 is an $^1$H-NMR analysis chart of a compound of this invention, obtained in Example 1.

Mass spectrometric analysis of Compound (Ia) showed M/Z of 534. Further, Compound (Ia) was structurally analyzed by IR measurement and $^1$H-NMR (400 MHz) measurement. The IR analysis chart is shown in FIG. 1, and the $^1$H-NMR analysis chart is shown in FIG. 2. In the IR analysis chart in FIG. 1, absorption based on the exterior of the C-H plane of a vinyl group was clearly observed at 943 cm$^{-1}$, whereby the presence of vinyl bonds was recognized.

The results of assignment of the $^1$H-NMR analysis chart in FIG. 2 are as follows.

| Peak No. | ppm | Assignment | Integration ratio |
| --- | --- | --- | --- |
| 1 | 6.45 | a | 1 |
| 2 | 6.52 | a | 1 |
| 3 | 6.82 | b | 4 |
| 4 | 7.0 | c | 2 |
| 5 | 7.3 | d | 1 |
| 6 | 7.35 | d | 1 |
| 7 | 7.6 | e | 4 |

The above analysis results showed that Compound (Ia) obtained in this Example was 1,4-bis[2-tetrathiaful-valen-2-yl)vinyl]benzene of the following formula.

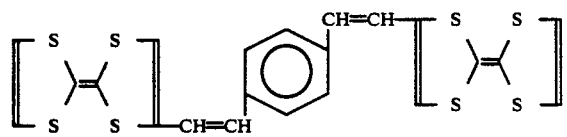

Compound (Ia) obtained in this Example 1 was measured for a first oxidation potential ($E_1$) and a second oxidation potential ($E_2$) by a cyclic voltammetry. The measurement conditions were as follows.

| Reference electrode | Ag/AgCl |
| --- | --- |
| Supporting electrolyte | n-Bu$_4$NBF$_4$ |
| Solvent | Chlorobenzene |
| Electrolyte concentration | 100 mmol/l |
| Sample compound concentration | 0.5 mmol/l |

Figure 3:
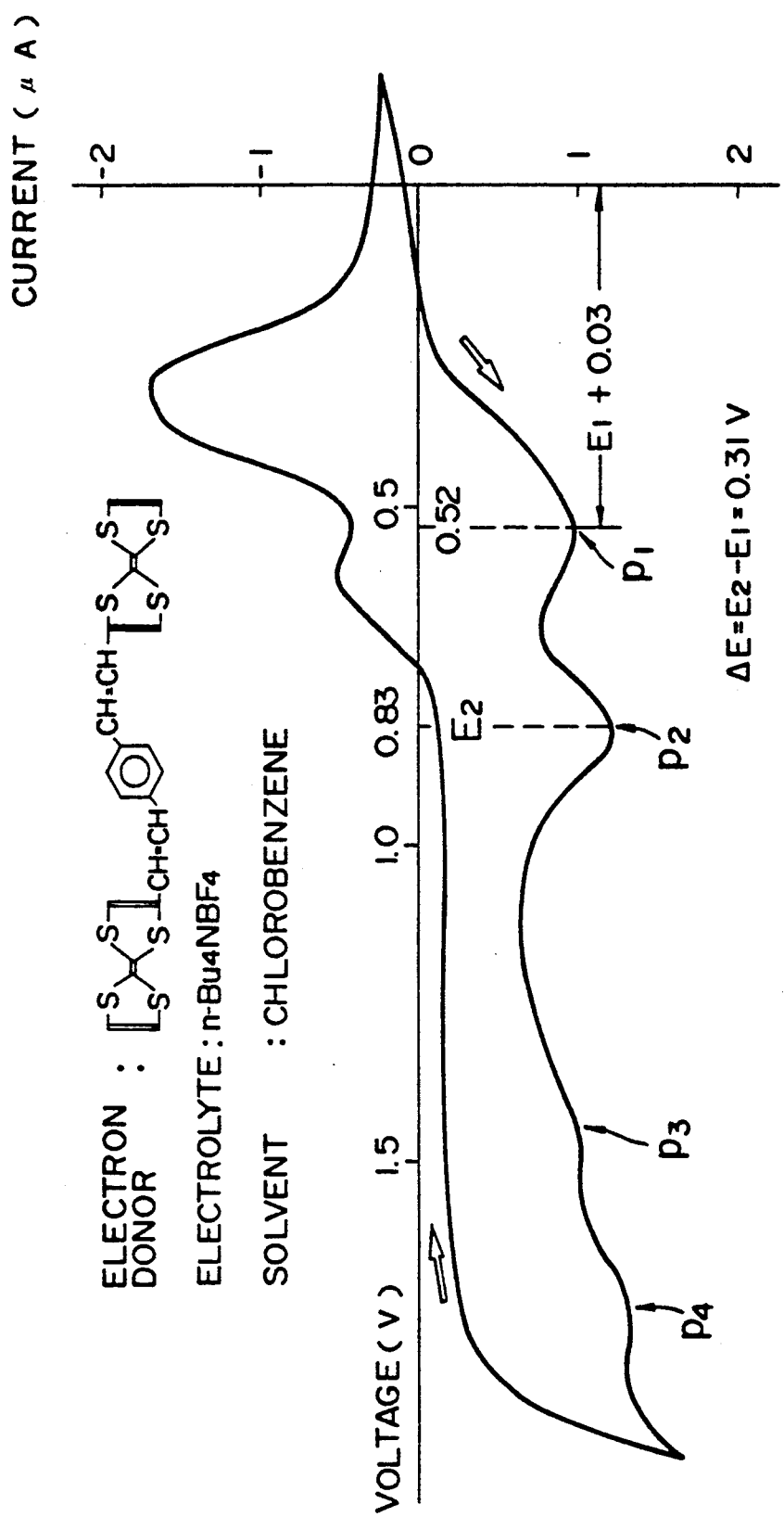
FIG. 3 is a cyclic voltammetry chart of a compound of this invention, obtained in Example 1.

FIG. 3 shows the results of the cyclic voltammetry. A current-voltage curve is drawn with the ordinate axis as current and the abscissa axis as voltage. In this case, a peak appears due to a sharp increase in current when the voltage is increased to a voltage at which a sample compound releases an electron. As is clearly shown in FIG. 4, the compound (Ia) of this Example 1 shows four peaks $p_1$, $p_2$, $p_3$ and $p_4$ since it releases four electrons one by one. And, a value obtained by subtracting 0.03 V from the voltage at the peak $p_1$ when a first electron is released is referred to as a first oxidation potential $E_1$, and the voltage at the peak $p_2$ is referred to as a second potential $E_2$.

It is known that a sample compound having a lower $E_1$ value is richer in electron donating nature. In Compound (Ia) of this Example 1, the $E_1$ value was 0.49 V as is clear in FIG. 3, and this value was lower than the $E_1$ value (1.0 V) of bisethyleneditetrathiafulvalene (BEDTTTF), the $E_1$ value (0.86 V) of tetramethyltetrathiafulvalene (TMTTF) and the $E_1$ value (0.85 V) of tetrathiafulvalene (TTF) shown in Comparative Example 1 which will be described later (see Table 1).

According to literature, a compound having a smaller difference ($\Delta E$) between the second oxidation potential $E_2$ and the first oxidation potential $E_1$ is generally a higher electron donor (see e.g. A. F. Gariito et al, Acc. Chem. Res., 7, 232 (1974); Z. Yoshida et al, Tetrahedron Lett., 24, 3473 (1983), M. R. Bryce, Tetrahedron Lett., 25, 2403 (1984). In Compound (Ia) of this Example 1, as is clear in FIG. 3, $\Delta E$ was 0.31 V, and this value is smaller than the $\Delta E$ (0.44 V) of BEDTTTF, the $\Delta E$ (0.53 V) of TMTTF and the $\Delta E$ (0.41 V) of TTF shown in Comparative Example 1 (see Table 1).

It is, therefore, clearly shown that Compound (Ia) of this Example 1 is richer in electron donating nature than the three known compounds in Comparative Example 1 since it has a lower $E_1$ and a smaller $\Delta E$ than these compounds.

Further, as is clear in Example 22 which will be described later, it was found that the compound (Ia) of this Example 1 was capable of forming a complex with an electron acceptor under a direct complex forming method.

EXAMPLE 2

Preparation of 1,4-bis[2-(tetrathiafulvalen-2-yl)vinyl]-2,5-dimethylbenzene [Compound (Ib)]

5 Grams (24.5 mmol) of 2,5-bis(chloromethyl)-p-xylene and 27 g (4 equivalent weight) of triphenylphosphine were added to 100 ml of DMF, and the resultant mixture was heated in an oil bath (bath temperature about 130° C.). After 50 minutes, while the reaction mixture was hot, it was filtered to obtain a reaction product, and the reaction product was washed with acetone, and dried to give 16.5 g of 2,5-dimethyl-p-xylylenebis(triphenylphosphonium chloride) (yield 92.6%).

Then, 2 g (2.75 mmol) of the above-obtained compound was suspended in 30 ml of THF. Then, under an argon gas current, 3.5 ml of a hexane solution of n-butyllithium (concentration 14% by weight) was added dropwise to the resultant- suspension over 5 minutes. Further, a solution containing 1.28 g (5.50 mmol) of 2-formyltetrathiafulvalene and 10 ml of THF was added dropwise, and the resultant mixture was allowed to react at room temperature for 6 hours with stirring. Thereafter, 3 ml of methanol was added to terminate the reaction, the solvent was distilled off, and the resultant product was washed with water, washed with methanol, recrystallized from DMF, filtered and dried to give 1.16 g of a brown solid (yield 68%). The brown solid obtained in this Example 2, i.e. Compound (Ib) had a decomposition temperature Td of 270° C. or was found to be excellent in thermal stability. Elemental analysis values thereof are as follows.

| | C | H | S |
| --- | --- | --- | --- |
| Calculated (%) | 51.2 | 3.2 | 45.6 |
| Found (%) | 51.4 | 3.3 | 45.3 |

Figure 4:
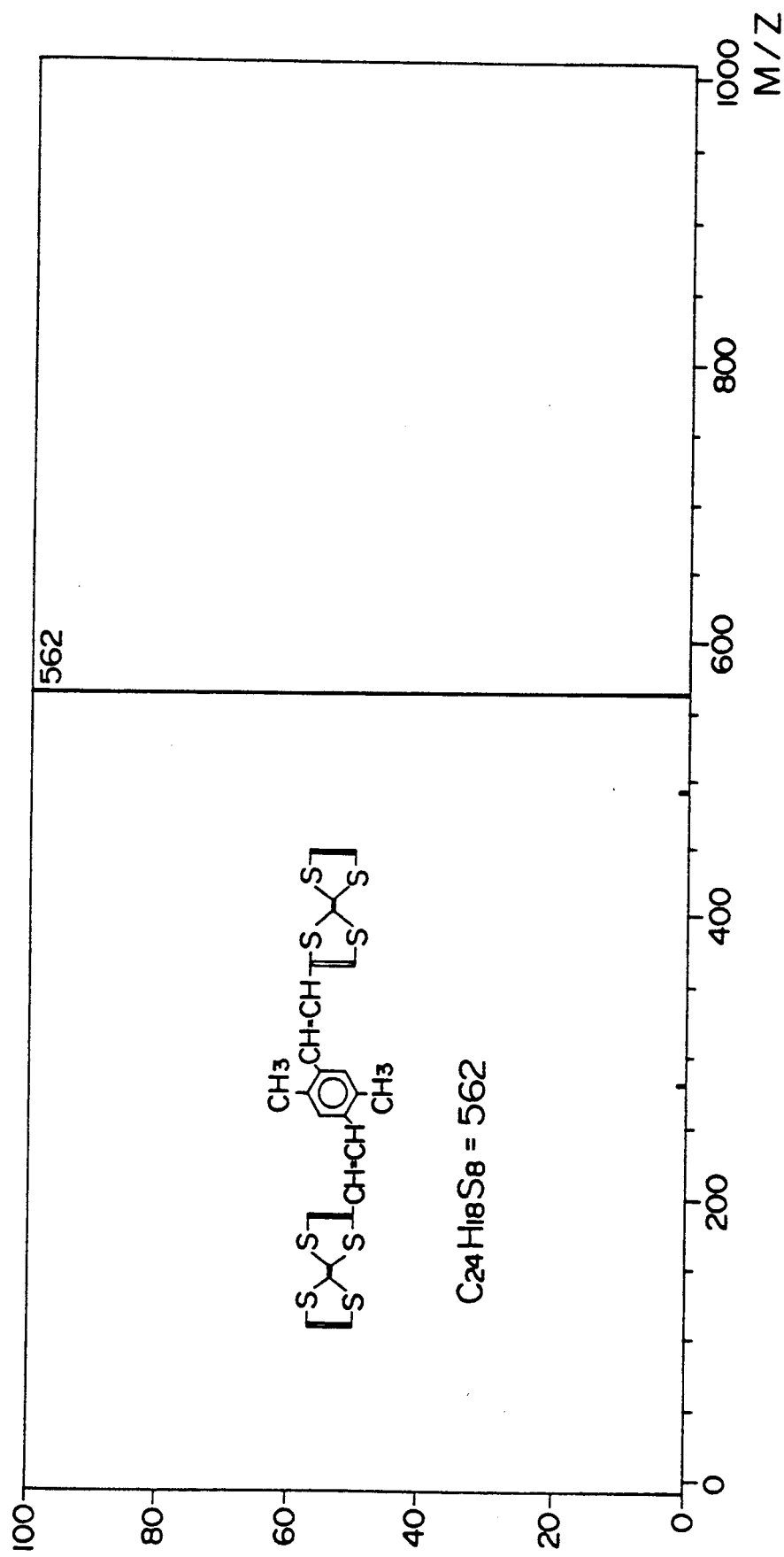
FIG. 4 is a mass spectrometry chart of a compound of this invention, obtained in Example 2.

FIG. 4 shows the mass spectrometry chart of Compound (Ib) obtained in this Example 2. As is clear in FIG. 4, Compound (Ib) had M/Z of 562.

The above results showed that Compound (Ib) was 1,4-bis[2-tetrathiafulvalen-2-yl)vinyl]-2,5-dimethylbenzene of the following formula.

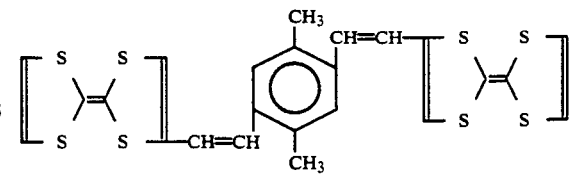

Compound (Ib) of this Example 2 was measured for $E_1$ and $\Delta E$ in the same manner as in the case of Compound (Ia) of Example 1 to show $E_1$ of 0.47 V and $\Delta E$ of 0.23, or found to be as rich in electron donating nature as Compound (Ia) of Example 1. As is clear in Example 22 which will be described later, it was also found that Compound (Ib) of this Example 1 was capable, similarly to Compound (Ia) of Example 1, of forming a complex with an electron acceptor under a direct complex forming method.

Figure 5:
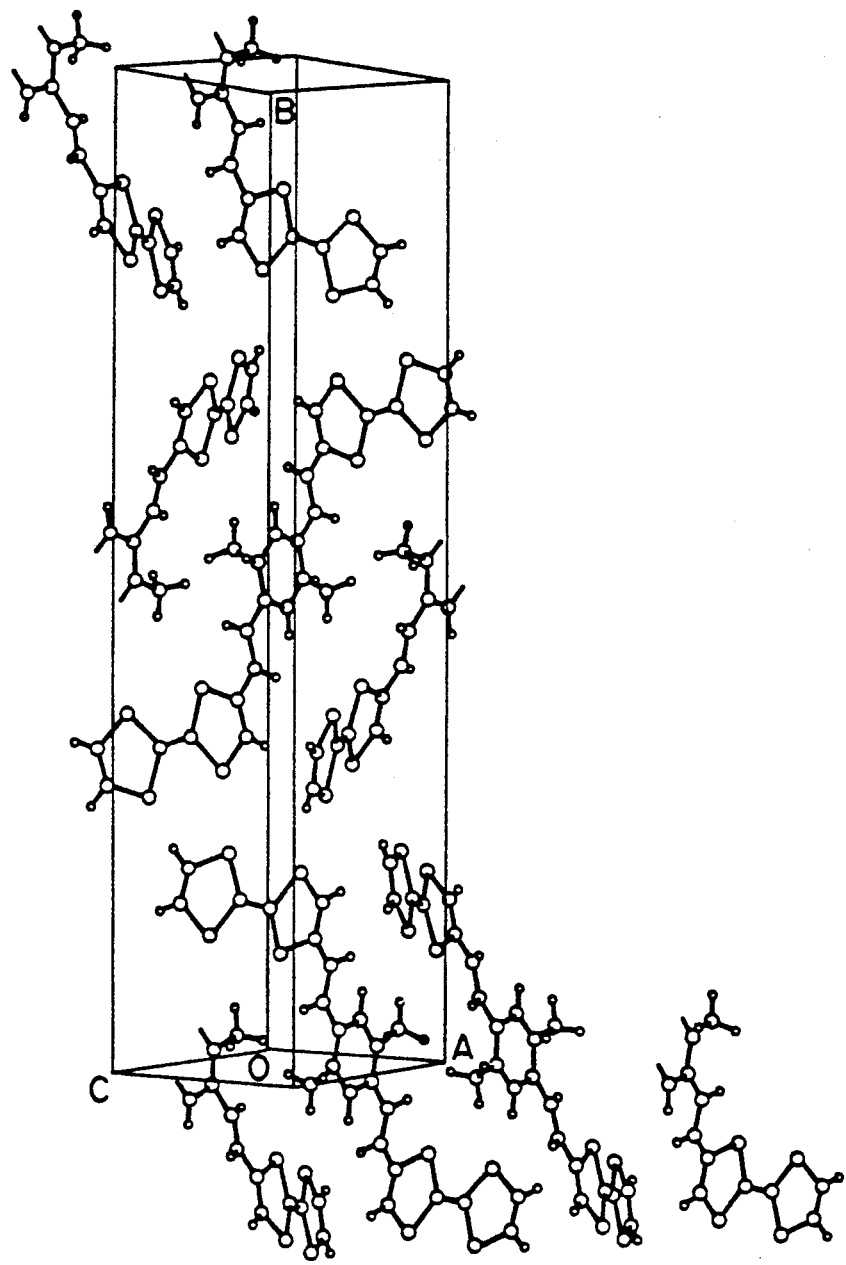
FIGS. 5 and 6 are structural analysis charts obtained by X-ray diffraction of single crystals of a compound of this invention, obtained in Example 2.
Figure 6:
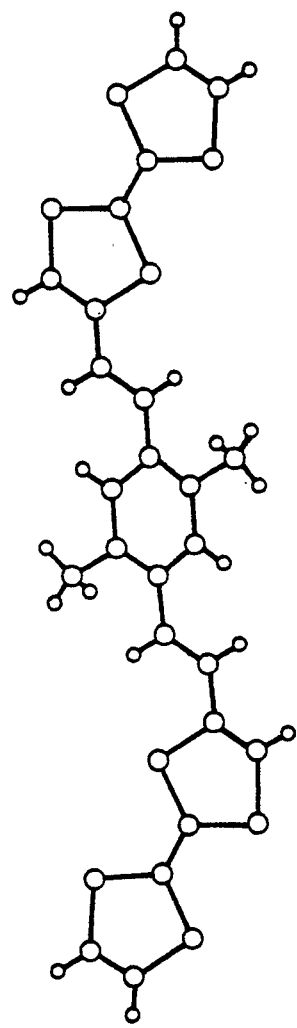

FIGS. 5 and 6 show structure analysis charts based on four-axis X-ray diffraction of single crystals of Compound (Ib) of this Example 2, measured by means of a four-axis X-ray diffractometer AFC-5R supplied by Rigaku Denki K.K.

On the basis of FIG. 5, the results of crystal structure analysis of this compound were as follows.

The compound had an R value of 0.053, and it was a single crystal having lattice parameters in which a=7.770 Å, b=34.949 Å, c=9.314 Å, $\beta$=91.972°, and V=2,528 Å$^3$, and a space group $P2_{1/c}$(#14). The chemical formula number Z in a unit lattice was 4. In addition, FIG. 6 shows an enlarged view of only one molecule of the compound.

EXAMPLE 3

Preparation of 1,4-bis[2-(tetraselenafulvalen-2-yl)vinyl]-2,5-dimethylbenzene [compound (Ic)]

1.96 Grams (5 mmol) of tetraselenafulvalene was dissolved in 100 ml of tetrahydrofuran, and the resultant mixture was cooled to $-65°$ C. Under an argon gas current, 20 ml of tetrahydrofuran solution of 0.535 g (5 mmol) of LDA (lithium diisopropylamide) was added dropwise over about 30 minutes, and the resultant mixture Was stirred for further 30 minutes. Thereafter, a solution formed was passed through a Teflon tube under argon pressure, and added to a mixture solution ($-70°$ C.) consisting of 50 mmol of DMF and 100 ml of tetrahydrofuran. Then, the resultant mixture was brought back to room temperature, and subjected, after water was added, to extraction with ether. The ether was evaporated, and the residue was purified by column chromatography to give 0.9 g (2.1 mmol) of 2-formyltetraselenafulvalene (melting point 127.4° C.).

On the other hand, 0.75 g (1.1 mmol) of p-xylylenebis(triphenylphosphonium chloride) was suspended in 15 ml of THF, and under argon gas current, 5 ml of a hexane solution of n-butyllithium (concentration 14%) was added dropwise, and then, a solution of 0.9 g (2.1 mmol) of the 2-formyltetraselenafulvalene in 10 ml of THF was added dropwise to the reaction solution. The resultant reaction solution was allowed to react by stirring it at room temperature for 6 hours. Thereafter, 50 ml of methanol was added dropwise to terminate the reaction, and the reaction solution was filtered. And, the resultant product was consecutively washed with methanol, with water, and with methanol, and dried to give 0.4 g of the intended Compound (Ic) (yield 39%).

Table I summarizes the thermal decomposition temperature Td of Compound (Ic), its elemental analysis values, its M/Z in mass spectrometry, its $E_1$ and $\Delta E$ determined by cyclic voltammetry, and its capability of directly forming a complex. As is clear in Table 1, Compound (Ic) had a thermal decomposition temperature Td of as high as 230° C., or was found to be excellent in thermal stability. Further, the elemental analysis values and M/Z in mass spectrometry showed that Compound (Ic) was 1,4-bis(2-(tetraselenafulvalen-2-yl)vinyl]-2,5-dimethylbenzene of the following formula.

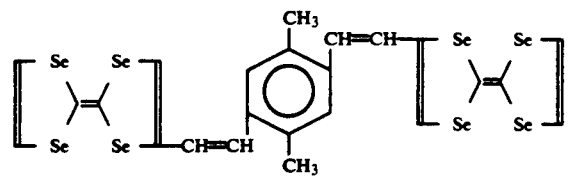

Compound (Ic) had $E_1$ of 0.57 V and $\Delta E$ of 0.2 V, or found to be rich in electron donating nature. As is detailed in Example 22 which will be described later, it was, also found that Compound (Ic) was also capable of forming a complex with an electron acceptor under a direct complex forming method.

EXAMPLE 4

Preparation of 1,4-bis[2-(3,6,7-trimethyltetraselenafulvalen-2-yl)vinyl]-benzene [Compound (Id)]

2 Grams (4.6 mmol) of tetramethylselenafulvalene was dissolved in 200 ml of anhydrous carbon tetrachloride, and 2 g of NBS (N-bromosuccinimide) and 0.3 g of benzoyl peroxide were added. The resultant mixture was gradually heated in an oil bath with stirring vigorously. The reaction was exothermic, and proceeded with releasing heat. After the heat release terminated, the reaction mixture was stirred further for 1 hour.

After the reaction mixture was cooled and filtered, the carbon tetrachloride was evaporated, and the residue was distilled under reduced pressure. Added to the distillate was 20 ml (161 mmol) of triethyl phosphite, and the resultant mixture was heated at 120° C. for 5 hours. The reaction mixture was filtered, followed by washing with dichloromethane and separation with a column, whereby a monoreactant alone was separated and recovered. This monoreactant was reacted with terephthalaldehyde according to an ordinary Wittig reaction (n-BuLi/THF system) to give 0.05 g of the intended Compound (Id) (yield 2%).

Table 1 summarizes the thermal decomposition temperature Td of Compound (Id), its elemental analysis values, its M/Z in mass spectrometry, its $E_1$ and $\Delta E$ determined by cyclic voltammetry, and its capability of directly forming a complex. As is clear in Table 1, Compound (Id) had a thermal decomposition temperature Td of as high as 245° C., or was found to be excellent in thermal stability. Further, the elemental analysis values and M/Z in mass spectrometry showed that Compound (Id) was 1,4-bisp8 2-(3,6,7-trimethyltetraselenafulvalen-2-yl)vinyl]-2,5-dimethylbenzene of the following formula.

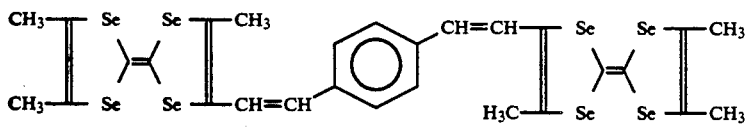

Compound (Id) had $E_1$ of 0.53 V and $\Delta E$ of 0.3 V, or found to be rich in electron donating nature. As is detailed in Example 22 which will be described later, it was also found that Compound (Id) was also capable of forming a complex with an electron acceptor under a direct complex forming method.

EXAMPLE 5

Preparation of 1,4-bis[2-(6,7-ethylenedithiotetrathiafulvalen-2-yl)vinyl]-2,5-dimethyl benzene [compound (Ie)]

30 Grams (0.12 mol) of dimethyl 1,3-dithiol-2-thion-4,5-dicarboxylate synthesized according to the method of G. C. Papavassiliou, et al [Synthetic Metals, Vol. 27 (1988) B-373-B378] was dissolved in 30 ml of hexamethylphosphorictriamide (HMPA), and 12.6 g (0.12 mol) of lithium bromide monohydrate was added. The resultant mixture was heated at 60° C. for 1 hour, the reaction mixture was allowed to cool to room temperature, 200 ml of water was added, and a yellow solid formed was separated by filtering and washed with water. The solid obtained was dried and recrystallized from carbon tetrachloride to give 16.2 g of yellow acicular crystals of methyl 1,3-dithiol-2-thione-4-carboxylate (yield 70%).

2.3 Grams (11.2 mmol) of 4,5-ethylenedithio-1,3-dithiol-2-one and 4.3 g (22.4 mmol) of methyl 1,3-dithiol-2-thion-4-carboxylate were dissolved in 30 ml of toluene, and 10 ml (60 mmol) of triethyl phosphite was added. The resultant mixture was refluxed in an argon gas current for 2 hours. Acicular crystals (2,3,6,7-bisethylenedithiotetra-thiafulvalene, 0.8 g) formed when the reaction mixture was allowed to cool to room temperature was removed by filtering, and the filtrate was concentrated and distilled under reduced pressure to remove $P(OEt)_3$. The remaining black solid was purified with column chromatography to give 0.8 g of a red solid of 2,3-ethylenedithio-6-methoxycarbonyltetrathiafulvalene (yield 20%).

4.9 Grams of a 70% toluene solution of sodium bis(2-methoxyethoxy)aluminum hydride (SMEAH) (containing 17.1 mmol of SMEAH) was dissolved in 6 ml of anhydrous toluene, and the resultant mixture was cooled to 0° C. under an argon gas current. A solution of 1.6 g (18.4 mmol) of anhydrous morpholin (MPL) in anhydrous toluene was slowly added dropwise to the mixture over 30 minutes to prepare an SMEAH-MPL mixed reagent.

2 Grams (5.7 mmol) of 2,3-ethylenedithio-6-methoxycarbonyltetrathiafulvalene was dissolved in 120 ml of anhydrous toluene, and the resultant mixture was cooled to 0° C. The above SMEAH-MPL mixed reagent was slowly added dropwise to the mixture over 30 minutes under an ar-on gas current. After the addition, the mixture was stirred at 0° C. for 30 minutes, and while the mixture had a temperature of 0° C., 2N sulfuric acid was added to acidify the mixture solution. Anhydrous magnesium sulfate was added to solidify a water phase, and the solution was filtered. The remaining solid was washed with dichloromethane, and these two liquids (filtrate and dichloromethane wash liquid) were together concentrated and purified by column chromatography to give 0.46 g of a red solid of 6,7-ethylenedithio-2-formyltetrathiafulvalene (m.p. 153° C., yield 25%).

0.28 Gram (0.369 mmol) of 2,5-dimethylxylylene-bistriphenylphosphonium was suspended in 20 ml of anhydrous THF, and at room temperature and under an argon gas current, 1.0 ml of a hexane solution of 15% n-butyllithium (containing 1.6 mmol of n-butyllithium) was added. After the resultant mixture was stirred at room temperature for 5 minutes, a solution of 0.25 g (0.78 mmol) of 6,7-ethylenedithio-2-formyltetrathiafulvalene in 20 ml of an anhydrous THF was added to the mixture, and the mixture was stirred at room temperature for 2 hours. An equivalent amount of methanol was added to terminate the reaction, and a solid formed was separated by filtering, and washed with methanol. The solid was recrystallized from DMF to give 80 mg of golden plate-like crystals of the intended Compound (Ie) (yield 28%).

Table 1 summarizes the thermal decomposition temperature Td of Compound (Ie), its elemental analysis values, its M/Z in mass spectrometry, its $E_1$ and $\Delta E$ determined by cyclic voltammetry, and its capability of directly forming a complex. As is clear in Table 1, Compound (Ie) had a thermal decomposition temperature Td of as high as 227° C., or was found to be excellent in thermal stability.

Figure 7:
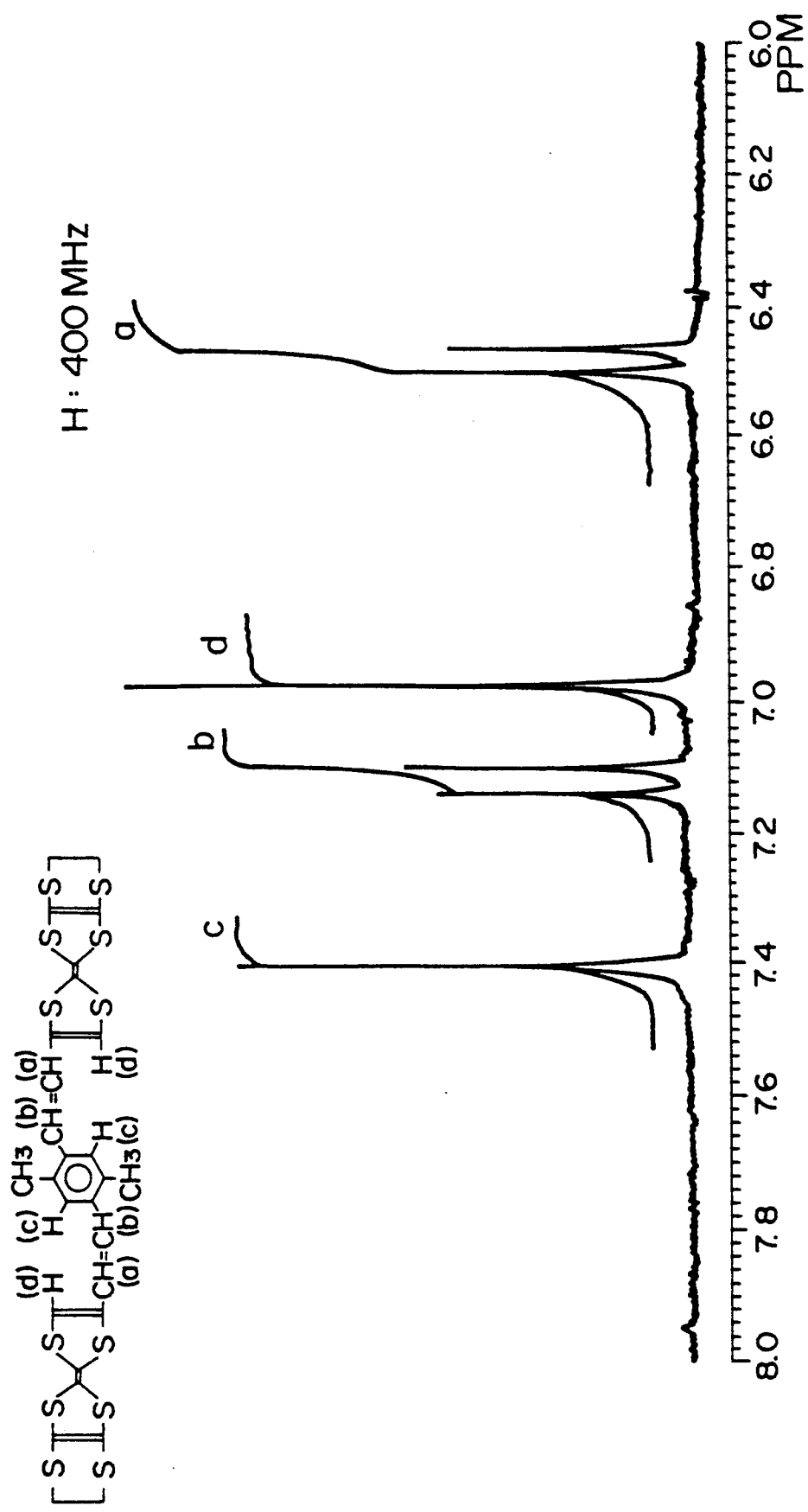
FIG. 7 is an $^1$H-NMR analysis chart of a compound of this invention, obtained in Example 5.

Further, the elemental analysis values, the M/Z in mass spectrometry and $^1$H-NMR shown in FIG. 7 showed that Compound (Ie) was 1,4-bis[2-(6,7-ethylenedithiotetrathia-fulvalen-2-yl)vinyl]-2,5-dimethylbenzene of the following formula.

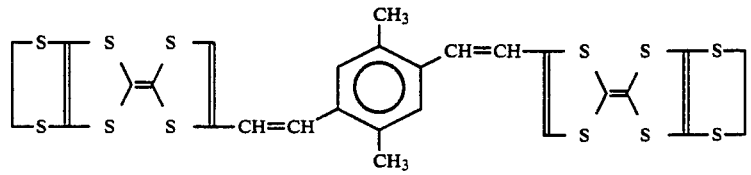

Compound (Ie) had $E_1$ of 0.55 V and $\Delta E$ of 0.26 V, or found to be rich in electron donating nature. As is detailed in Example 22 which will be described later, it was also found that Compound (Ie) was also capable of forming a complex with an electron acceptor under a direct complex forming method.

Figure 8:
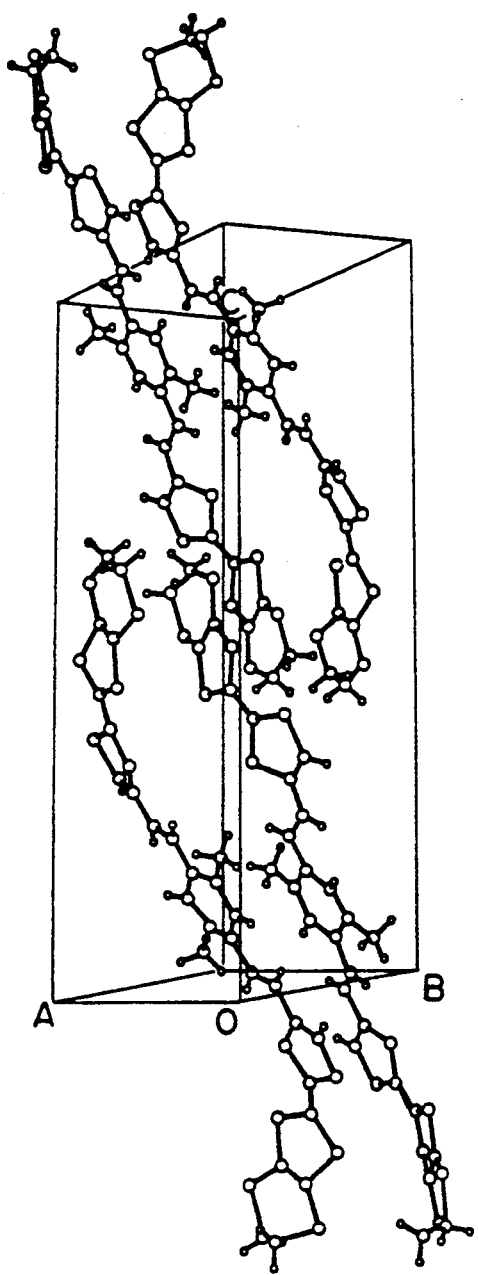
FIGS. 8 and 9 are structural analysis charts obtained by X-ray diffraction of single crystals of a compound of this invention, obtained in Example. 5.
Figure 9:
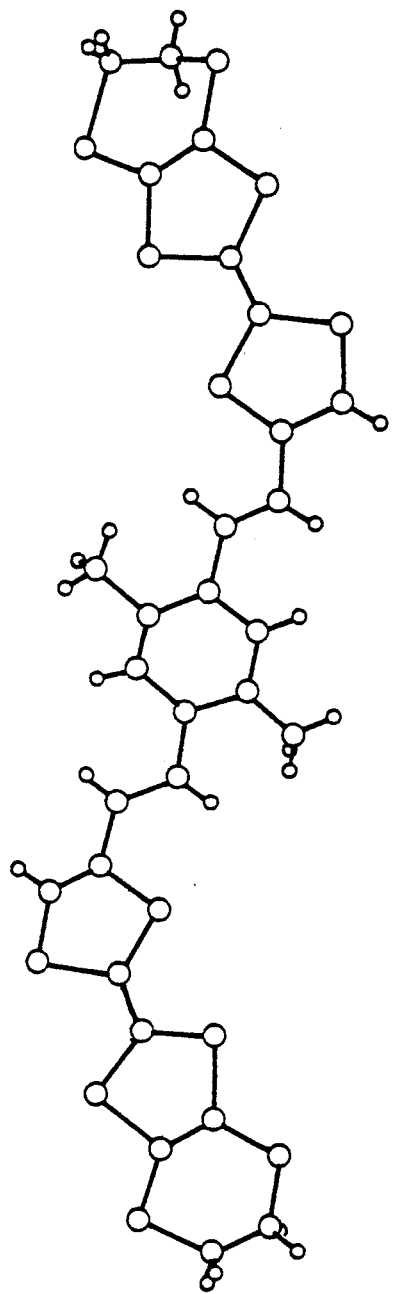

FIGS. 8 and 9 are structural analysis charts obtained by X-ray diffraction of single crystals of Compound (Ie)

obtained in this Example 5. On the basis of FIG. 8, the structural analysis of this Compound (Ie) are as follows.

Compound (Ie) had an R value of 0.071, and it was a single crystal having lattice parameters in which a=8.287 Å, b=13.803 Å, c=27.54 Å, $\beta$=92.94°, and V=3,146 Å$^3$ and a space group P2$_{1/c}$ (#14). The chemical formula number Z in a unit lattice was 4. In addition, FIG. 9 shows an enlarged view of only one molecule of this Compound.

EXAMPLE 6

Preparation of 1,4-bis[2-(6,7-bismethylthiotetrathiafulvalen-2-yl)vinyl]-2,5-dimethylbenzene

[Compound (If)]

Dimethyltetrathiafulvalene 2,3-bismethylthio-6,7-dicarboxylate was synthesized according to the method of G. C. Papavassiliou, et al [Synthetic Metals, Vol. 27 (1988) B373-B378].

That is, 5.75 g (27.4 mmol) of 4,5-dimethylthio-1,3-dithiol-2-one and 13.7 g (54.8 mmol) of methyl 1,3-dithiol-2-thion-4-carboxylate were dissolved in 120 ml of toluene, and 60 ml (360 mmol) of triethyl phosphite was added. The resultant mixture was refluxed in an argon gas current for 7 hours. The reaction mixture was allowed to cool to room temperature, and the filtrate was concentrated land distilled under reduced pressure to remove triethyl phosphite. Added to the remaining solid was 100 ml of methanol, and the resultant mixture was filtered. The filtrate was purified by column chromatography to give 1.32 g (3.2 mmol) of a dense reddish brown solid of dimethyltetrathiafulvalene 2,3-dimethylthio-6,7-dicarboxylate (yield 11.7%).

Then, 1.32 Grams (3.2 mmol) of dimethyltetrathiafulvalene 2,3-bismethylthio-6.7-dicarboxylate was dissolved in 50 ml of hexamethylphosphoricamide (HMPA), and 2.15 g (24.8 mmol) of lithium bromide monohydrate was added. The resultant mixture was heated at 150° C. for 15 minutes. The reaction mixture was allowed to cool to room temperature, 400 ml of water was added, and the resultant mixture was subjected to extraction with dichloromethane. The extract was drid over magnesium sulfate and subjected to evaporation. Further, the residue was heated in an oil bath at 100° C., HMPA was distilled off under reduced pressure, and dichloromethane was added. The resultant mixture was purified by a silica column to give 0.546 g (1.84 mmol) of of 2,3-dimethylthiotetrathiafulvalene (yield 57.5%). Added to the entire amount thereof were 0.257 g (2.21 mmol) of ethylenediamine and 40 ml of ether. And, the resultant mixture was cooled to −78° C. with dry ice-ethanol, and 1.26 ml of a hexane solution of 15% n-butyllithium (containing 2.02 mmol of n-butyllithium) was added thereto dropwise over 10 minutes. The mixture was further stirred for 1 hour, and 1.4 ml (18.4 mmol) of DMF and 40 ml of ether which were cooled to −78° C. were forced into the mixture under argon pressure through a Teflon tube. Then, the dry ice bath was removed to bring the resultant suspension back to room temperature. The suspension was poured into 250 ml of pure water, and the mixture was subjected to extraction with ether, followed by drying with magnesium sulfate and purification by column chromatography, whereby there was obtained 0.26 g (0.8 mmol) of 2,3-bismethylthio-6-formyltetrathiafulvalene (yield 43.5%).

0.29 Gram (0.4 mmol) of 2,5-dimethylxylylenebistriphenylphosphonium chloride was suspended in 20 ml of anhydrous THF, and 1.0 ml of a hexane solution of 15% n-butyllithium (containing 1.6 mmol of n-butyllithium) was added at room temperature under an argon gas current. After the resultant mixture was stirred at room temperature for 5 minutes, a solution of 0.26 g (0.8 mmol) of 2,3-bismethylthio-6-formyltetrathiafulvalene in 20 ml of anhydrous THF was added, and the mixture was stirred at room temperature for 2 hours. An equal amount of methanol was added to terminate the reaction, and the resultant solid was separated by filtering and washed with methanol to give 90 mg of the intended Compound (If) (yield 30%).

Table 1 summarizes the thermal decomposition temperature Td of Compound (If), its elemental analysis values, its M/Z in mass spectrometry, its $E_1$ and $\Delta E$ determined by cyclic voltammetry, and its capability of directly forming a complex. As is clear in Table 1, Compound (If) had a thermal decomposition temperature of as high as 236° C., or was found to be excellent in thermal stability.

Figure 10:
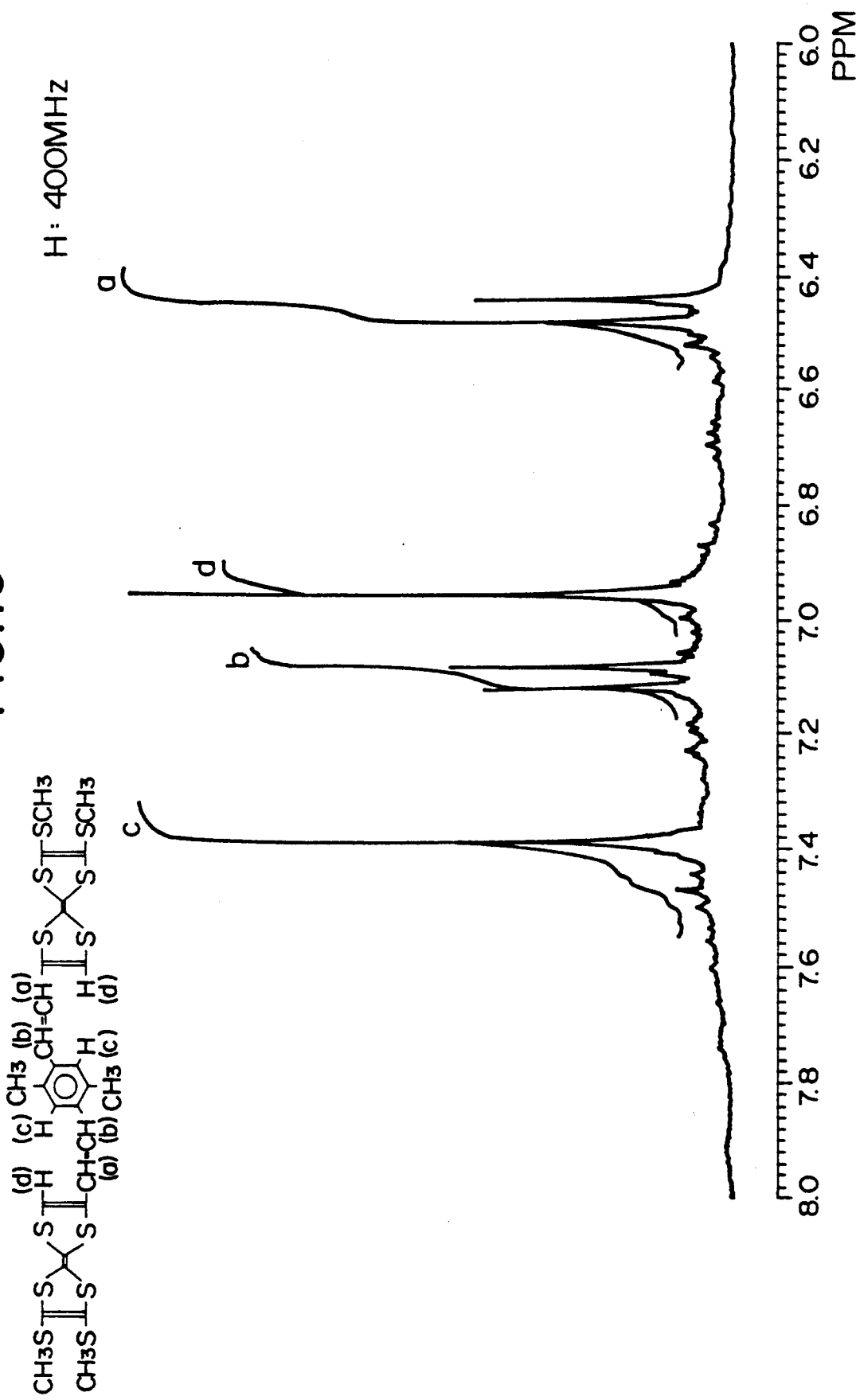
FIG. 10 is an $^1$H-NMR analysis chart of a compound of this invention, obtained in Example 6.

Further, the elemental analysis values, the M/Z in mass spectrometry and $^1$H-NMR shown in FIG. 10 showed that Compound (If) was 1.4-bis(2-(6,7-bismethylthiotetrathiafulvalen-2-yl)vinyl]-2,5-dimethylbenzene of the following formula.

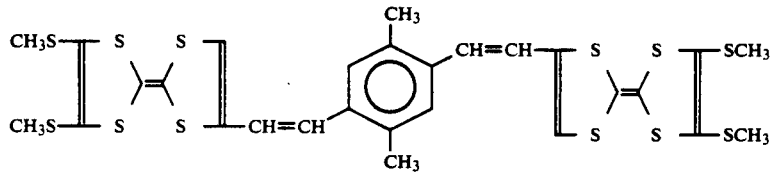

Compound (If) had $E_1$ of 0.52 V and $\Delta E$ of 0.32 V. or found to be rich in electron donating nature. As is detailed in Example 22 which will be described later, it was also found that Compound (If) was also capable of forming a complex with an electron acceptor under a direct complex forming method.

EXAMPLE 7

Preparation of 1,4-bis[2-(tetrathiafulvalen-2-yl)vinyl]-2-methoxybenzene [Compound (Ig)]

1,4-Dibromomethyl-2-methoxybenzene was synthesized according to the method of Marcel Hibert, et al (J. Org. Chem. 45, 4,496–4,498 (1980)]. Added thereto was triphenylphosphine, and the resultant mixture was heated in DMF. Bis-1,4-(triphenylphosphoniumbromo)-2-methoxybenzene precipitated was separated by filtering, dried and used in the following reaction. That is, 1.0 g (1.2 mmol) of this bis-1,4-(triphenylphosphoniumbromo)-2-methoxybenzene was suspended in 15 ml of THF, and under an argon current, 5 ml of a hexane solution of n-butyllithium (concentration 14%) was added dropwise. Added dropwise to the resultant mixture was a solution of 0.6 g (2.6 mmol) of 2-formyltetrathiafulvalene in 10 ml of THF, and the mixture was stirred at room temperature for 6 hours. Then, 50 ml of methanol was added dropwise to terminate the reaction, followed by filtering, washing with methanol, washing with water, washing with methanol, recrystallization from DMF and drying, whereby 0.3 g of the intended Compound (Ig) was obtained (yield 41%).

Table 1 summarizes the thermal decomposition temperature Td of Compound (Ig), its elemental analysis values, its M/Z in mass spectrometry, its $E_1$ and $\Delta E$ determined by cyclic voltammetry, and its capability of directly forming a complex. As is clear in Table 1, Compound (Ig) had a thermal decomposition temperature Td of as high as 220° C., or was found to be excellent in thermal stability. Further, the elemental analysis values and the M/Z in mass spectrometry showed that Compound (Ig) was 1,4-bis[2-tetrathiafulvalen-2-yl)vinyl]-2-methoxybenzene of the following formula.

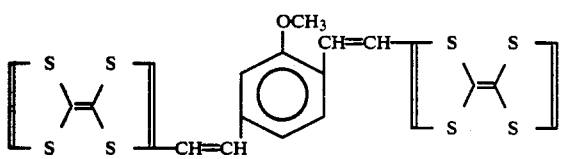

Compound (Ig) had $E_1$ of 0.46 V and $\Delta E$ of 0.31 V. or found to be rich in electron donating nature. As is detailed in Example 22 which will be described later, it was also found that Compound (Ig) was also capable of forming a complex with an electron acceptor under a direct complex forming method.

EXAMPLE 8

Preparation of 1,4-bis[2-(tetrathiafulvalen-2-yl)vinyl]-2-chlorobenzene [Compound (Ih)]

A 200 ml round-bottomed flask was charged with 7.0 g (50 mmol) of 2-chloro-p-xylene and 22.8 g (0.13 mol) of N-bromosuccinimide, and further charged with 100 ml of carbon tetrachloride. 1 Gram (4 mmol) of benzoyl peroxide was added, and the resultant mixture was gradually heated in an oil bath which was preliminarily heated to 90° C. When about five minutes passed, the mixture started a reaction, and the mixture was heat-refluxed for 80 minutes. The reaction mixture was allowed to cool, and the carbon tetrachloride was distilled off with a rotary evaporator. Added to the residue were 100 ml of THF and 30 g (114 mmol) of triphenylphosphine, and the mixture was heat-refluxed for 3 hours. A solid precipitated was separated, washed with a small amount of THF, and recrystallized from methanol to give 8.6 g (11 mmol) of the phosphonium salt (yield 22%). A 100 ml flask was subjected to replacement with argon, and charged with 1.6 g (1.9 mmol) of the above phosphonium salt and 10 ml of anhydrous THF. When a solution of 0.4 g (3.6 mmol) of potassium tert-butoxide in.10 ml of anhydrous THF was added dropwise with stirring, the resultant mixture was colored in dark reddish brown as a whole. This mixture was stirred at room temperature for 15 minutes, and a solution of 1 g (4.3 mmol) of 2-formyltetrathiafulvalene in 10 ml of anhydrous THF was added dropwise. The resultant mixture was stirred for 30 minutes, and then, a small amount of methanol and water was added to allow an excess amount of alkali to react, followed by washing with a large amount of methanol and filtering.

100 Milliliters of dichloromethane was added, and the mixture was filtered and subjected to a silica column. Then, the solvent was dried and distilled off to give 0.18 g of the intended Compound (Ih) (yield 17%).

Table 1 summarizes the thermal decomposition temperature Td of Compound (Ih), its elemental analysis values, its M/Z in mass spectrometry, its $E_1$ and $\Delta E$ determined by cyclic voltammetry, and its capability of directly forming a complex. As is clear in Table 1, Compound (Ih) had a thermal decomposition temperature of as high as 248° C., or was found to be excellent in thermal stability.

Figure 11:
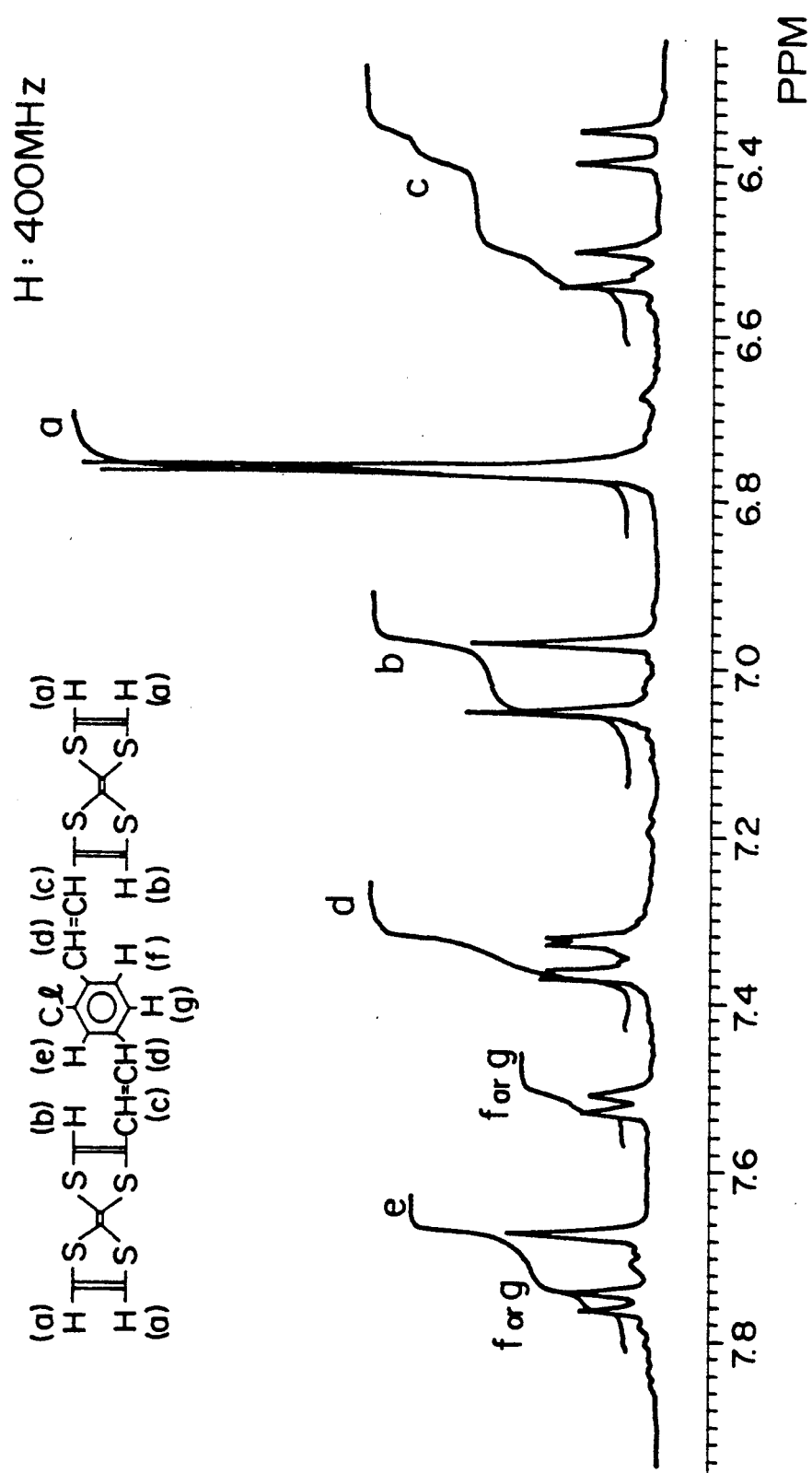
FIG. 11 is an $^1$H-NMR analysis chart of a compound of this invention, obtained in Example 8.

Further, the elemental analysis values, the M/Z in mass spectrometry and $^1$H-NMR shown in FIG. 11 showed that Compound (Ih) was 1,4-bis(2-(tetrathiafulvalen-2-yl)vinyl]-2-chlorobenzene of the following formula.

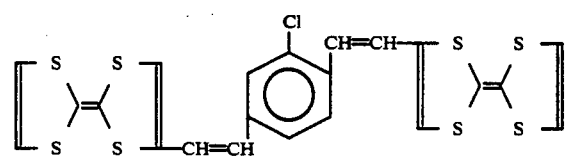

Compound (Ih) had $E_1$ of 0.49 V and $\Delta E$ of 0.31 V, or found to be rich in electron donating nature. As is detailed in Example 22 which will be described later, it was also found that Compound (Ih) was also capable of forming a complex with an electron acceptor under a direct complex forming method.

EXAMPLE 9

Preparation of 1,4-bis[2-(3,6,7-trimethyltetrathiafulvalen-2-yl)vinyl]benzene [Compound (Ii)

5 Grams (19 mmol) of tetramethyltetrathiafulvalene was dissolved in 20 ml of anhydrous carbon tetrachloride, and 3.4 g of NBS (N-bromosuccinimide) and 0.5 g of benzoyl peroxide were added. The resultant mixture was heated in an oil bath with stirring vigorously. The reaction proceeded with generating heat. After the heat generation stopped, the reaction mixture was further stirred for 1 hour. The reaction mixture was cooled and filtered, and the carbon tetrachloride was evaporated. The residue was distilled under reduced pressure. Added to the resultant distillate was 50 ml (403 mmol) of triethylphosphite, and the resultant mixture was heated at 120° C. for 5 hours. The reaction liquid was filtered, followed by washing with dichloromethane and separation with a column, whereby a monoreactant alone was recovered. This monoreactant and terephthalaldehyde were reacted with each other according to a conventional Wittig reaction (n-BuLi/THF system) to give 0.2 g of the intended Compound (Ii) (yield 3%).

Table 1 summarizes the thermal decomposition temperature Td of Compound (Ii), its elemental analysis values, its M/Z in mass spectrometry, its $E_1$ and $\Delta E$ determined by cyclic voltammetry, and its capability of directly forming a complex. As is clear in Table 1, Compound (Ii) had a thermal decomposition temperature Td of as high as 270° C., or was found to be excellent in thermal stability. Further, the elemental analysis values and the M/Z in mass spectrometry showed that Compound (Ii) was 1,4-bis[2-(3,6,7-trimethyltetrathiafulvalen-2-yl)vinyl]benzene of the following formula.

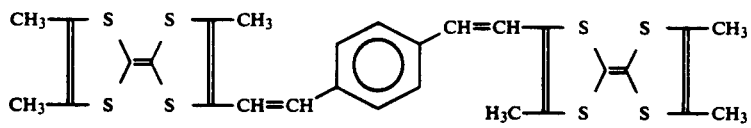

Compound (Ii) had $E_1$ of 0.48 V and $\Delta E$ of 0.32 V, or found to be rich in electron donating nature. As is detailed in Example 22 which will be described later, it was also found that Compound (Ii) was also capable of forming a complex with an electron acceptor under a direct complex forming method.

EXAMPLE 10

Preparation of 1-[2-(tetrathiafulvalen-2-vinyl]-4-[2-(6,7-methylenedithiotetrathiafulvalen-2-yl)vinyl]-2,5-dimethylbenzene [Compound (Ij)]

A 500 ml three-necked round-bottomed flask was charged with 0.3 g (1.3 mmol) of 2-formyltetrathiafulvalene and 0.94 g (1.3 mmol) of 2,5-dimethylxylylenebistriphenylphosphonium chloride, and under an argon atmosphere, 200 ml of anhydrous 2-propanol was added. While the resultant mixture was heated in a hot water bath, it was stirred with a mechanical stirrer until a solution was formed. The solution was allowed to cool, and while the solution was vigorously stirred, a 2-propanol solution of lithium 2-propoxide [prepared by adding 0.8 ml of n-butyllithium-hexane solution (containing 1.3 mmol of n-butyllithium) dropwise to 100 ml of 2-propanol] was added dropwise with a dropping funnel over 2 hours. Thereafter, the resultant mixture was stirred at room temperature for 2 hours. The reaction liquid became reddish orange to form a precipitate. The reaction mixture was subjected to suction filtration, and the filtrate was concentrated to about 10 ml by distilling off the solvent with a rotary evaporator. The filtrate was allowed to stand to precipitate a solid by crystallization, and the solid was separated by filtering, washed with a small amount of 2-propanol, and dried under vacuum to give 480 mg (0.74 mmol) of [2,5-dimethyl-4-(2-tetrathiafulvalenylethenyl)]benzyltriphenylphosphonium chloride (yield 57%).

Then, 2,3-methylenedithio-6,7-dimethoxycarbonyltetrathiafulvalene was synthesized according to the method of G. C. Papavassiliou, et al [Synthetic Metals, Vol. 27 (1988) B373-B378].

That is, 3.9 g (20.0 mmol) of 4,5-methylenedithio-1,3-dithiol-2-.one and 10 g (40 mmol) of dimethyl 1,3-dithiol-2-thion-4,5-dicarboxylate were dissolved in 80 ml of toluene, and 40 ml (240 mmol) of triethyl phosphite was added. The resultant mixture was refluxed in an argon gas current for 2 hours. The reaction mixture was allowed to cool to room temperature, concentrated and distilled under reduced pressure to remove triethyl phosphite. Added to the remaining liquid was 100 ml of methanol to precipitate a solid, and the solid was separated by filtering, and purified by column chromatography to give 2.7 g of a red solid of 2,3-methylenedithio-6,7-dimethoxycarbonyltetrathiafulvalene (yield 34%).

Then, 2.7 g (6.7 mmol) of the so-obtained 2,3-methylenedithio-6,7-dimethoxycarbonyltetrathiafulvalene was dissolved in 30 ml of hexamethylphosphoricamide (HMPA), 1.1 g (10 mmol) of lithium bromide monohydrate was added, and the resultant mixture was heated at 80° C. for 30 minutes. The reaction mixture was allowed to cool to room temperature, 100 ml of methanol was added, and a red solid formed was separated by filtering and washed with methanol. The red solid was dried to give 2.1 g of a red crystal of 2,3-methylenedithio-6-methoxycarbonyltetrathiafulvalene (melting point 190° C., yield 93%). 4.9 Grams (17.1 mmol) of a toluene solution of 70% sodium bis(2-methoxyethoxy)aluminum hydroxide (SMEAH) was dissolved in 6 ml of anhydrous toluene, and the resultant mixture was cooled to 0° C. under an argon gas current. A solution of 1.6 g (18.4 mmol) of anhydrous morpholine (MPL) in anhydrous-toluene was slowly added to the above mixture over 30 minutes. The resultant mixture was stirred at 0° C. for about 10 minutes until occurrence of foam ceased, whereby an SMEAH-MPL mixed reagent was prepared. 2.03 Grams (6 mmol) of 2,3-methylenedithio-6-methoxycarbonyltetrathiafulvalene was dissolved in 120 ml of anhydrous toluene, and the resultant mixture was cooled to 0° C. Under an argon gas current, the above-prepared SMEAH-MPL mixed reagent was slowly added dropwise thereto. The resultant mixture was stirred at 0° C. for 30 minutes, and while the solution had a temperature of 0° C., 2N sulfuric acid was added to acidify the solution. Anhydrous magnesium sulfate was added to solidify the water phase of the solution. The resultant mixture solution was filtered, and the remaining solid was washed with dichloromethane. The former filtrate and the wash liquid were together concentrated and purified by column chromatography (silica gel/n-hexane:dichloromethane=1:1) to give 0.28 g of a red solid of 6,7-methylenedithio-2-formyltetrathiafulvalene (yield 15%).

0.4 Gram (0.62 mmol) of the previously synthesized [2,5-dimethyl-4-(2-tetrathiafulvalenylethenyl)]benzyltriphenylphosphonium chloride was weighed out, and suspended in 10 ml of THF, and under an argon gas current, 0.8 ml of a hexane solution of n-butyllithium (containing 1.24 mmol of n-butyllithium) was added dropwise to the suspension. After 5 minutes, 0.19 g (0.62 mmol) of 6,7-methylenedithio-2-formyltetrathiafulvalene was added. After 1 hour, 50 ml of methanol was added to precipitate a brown solid, followed by washing with methanol, filtering and drying, whereby 0.2 g of the intended Compound (Ij) was obtained (yield 51%).

Table 1 summarizes the thermal decomposition temperature Td of Compound (Ij), its elemental analysis values, its M/Z in mass spectrometry, its $E_1$ and $\Delta E$ determined by cyclic voltammetry, and its capability of directly forming a complex. As is clear in Table 1, Compound (Ij) had a thermal decomposition temperature of as high as 215° C., or was found to be excellent in thermal stability.

Further, the elemental analysis values and the M/Z in mass spectrometry showed that Compound (Ij) was 1-[2-(tetrathiafulvalen-2-yl)vinyl]-4(2-(6,7-methylenedithiotetrathiafulvalen-2-yl)vinyl]-2,5-dimethylbenzene of the following formula.

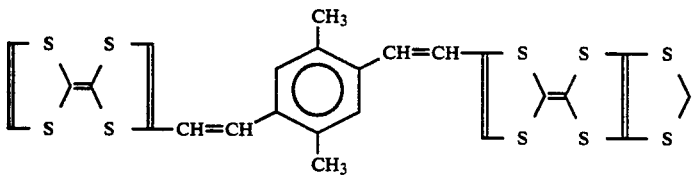

Compound (Ij) had $E_1$ of 0.50 V and $\Delta E$ of 0.28. V, or found to be rich in electron donating nature. As is detailed in Example 22 which will be described later, it was also found that Compound (Ij) was also capable of forming a complex with an electron acceptor under a direct complex forming method.

EXAMPLE 11

Preparation of 1-[2-(tetrathiafulvalen-2-yl)vinyl]-4-[2-(6,7-ethylenedithiotetrathiafulvalen-2-yl)vinyl]-2,5-dimethylbenzene [Compound (Ik)]

2 Grams (3.1 mmol) of (2,5-dimethyl-4-(2-tetrathiafulvalenylethenyl)]benzyltriphenylphosphonium chloride prepared in the same manner as in Example 10 was suspended in 50 ml of THF, and under an argon current, 4 ml of a hexane solution of n-butyllithium (containing 6.2 mmol of n-butyllithium) was added dropwise. After 5 minutes, 1 g (3.1 mmol) of 2,3-ethylenedithio-6-formyltetrathiafulvalene was added. After 1 hour, 200 ml of methanol was added to precipitate a brown solid, followed by washing with methanol, filtering and drying, whereby 0.9 g of the intended Compound (Ik) was obtained (yield 46%).

Table 1 summarizes the thermal decomposition temperature Td of Compound (Ik), its elemental analysis values, its M/Z in mass spectrometry, its $E_1$ and $\Delta E$ determined by cyclic voltammetry, and its capability of directly forming a complex. As is clear in Table 1, Compound (Ik) had a thermal decomposition temperature of as high as 210° C., or was found to be excellent in thermal stability.

Figure 12:
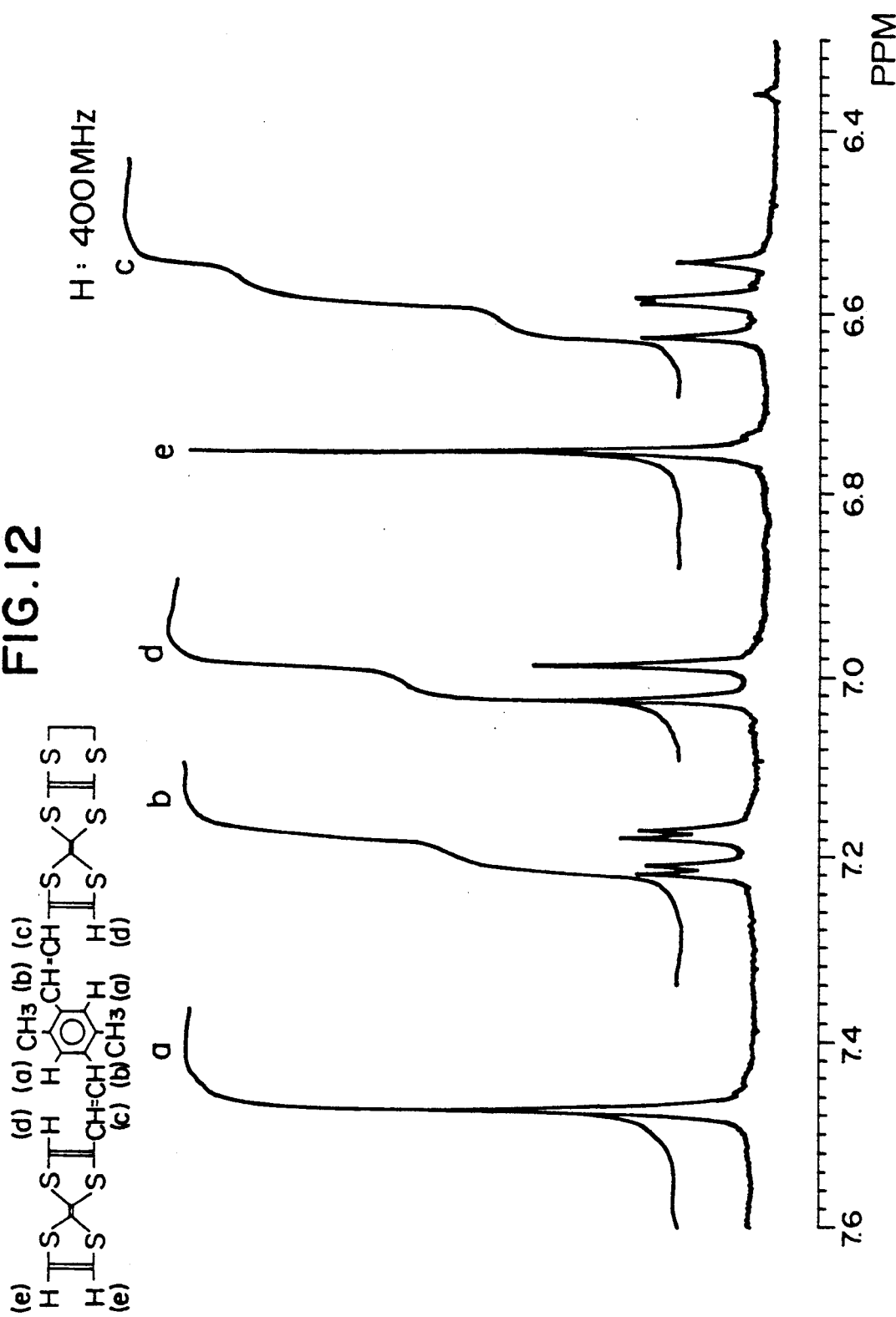
FIG. 12 is an $^1$H-NMR analysis chart of a compound of this invention, obtained in Example 11.

Further, the elemental analysis values, the M/Z in mass spectrometry and $^1$H-NMR shown in FIG. 12 showed that Compound (Ik) was 1-[2-(tetrathiafulvalen-2-yl)vinyl]-4-(2-(6,7-ethylenedithiotetrathiafulvalen-2-yl)vinyl]-2,5-dimethylbenzene of the following formula.

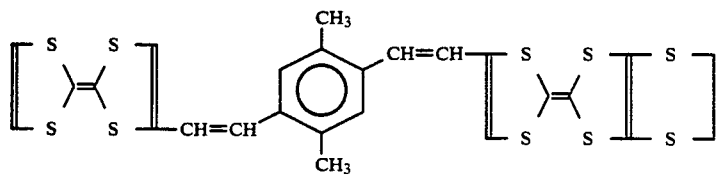

Compound (Ik) had $E_1$ of 0.52 V and $\Delta E$ of 0.30 V, or found to be rich in electron donating nature. As is detailed in Example 22 which will be described later, it was also found that Compound (Ik) was also capable of forming a complex with an electron acceptor under a direct complex forming method.

EXAMPLE 12

Preparation of 1-[2-(tetrathiafulvalen-2-yl)vinyl]-4-[2-(tetraselenafulvalen-2-yl)vinyl]-2,5-dimethylbenzene [Compound (Il)]

[2,5-Dimethyl-4-(2-tetrathiafulvalenylethenyl]-benzyltriphenylphosphonium chloride prepared in the same manner as in Example 10 and 2-formyltetraselenafulvalene synthesized in the same manner as in Example 3 were reacted with each other according to a Wittig reaction (n-BuLi/THF system) to give 0.3 g of the intended Compound (Il) (yield 50%).

Table 1 summarizes the thermal decomposition temperature Td of Compound (Il), its elemental analysis values, its M/Z in mass spectrometry, its $E_1$ and $\Delta E$ determined by cyclic voltammetry, and its capability of directly forming a complex. As is clear in Table 1, Compound (Il) had a thermal decomposition temperature Td of as high as 242° C., or was found to be excellent in thermal stability.

Further, the elemental analysis values and the M/Z in mass spectrometry showed that Compound (Il) was 1-[2-(tetrathiafulvalen-2-yl)vinyl]-4-(2-(tetraselenafulvalen-2-yl)vinyl]-2,5-dimethylbenzene of the following formula.

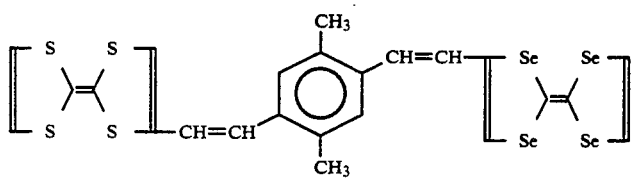

Compound (Il) had $E_1$ of 0.53 V and $\Delta E$ of 0.28 V, or found to be rich in electron donating nature. As is detailed in Example 22 which will be described later, it was also found that Compound (Il) was also capable of forming a complex with an electron acceptor under a direct complex forming method.

EXAMPLE 13

Preparation of 1,4-bis[2-(tetrathiafulvalen-2-yl)vinyl]-2,5-dimethoxybenzene [Compound (Im)]

2,5-Dimethoxy-1,4-bis(chloromethyl)benzene was synthesized according to the method described in Bull. Chem. Soc. Jpn. 48(2), 497–504.

1.41 Grams (6.0 mmol) of 2,5-dimethoxy-1,4-bis(chloromethyl)benzene and 3.78 g (14.4 mmol) of triphenylphosphine were added to 20 ml of DMF, and the resultant mixture was stirred at 100° C. for 2 hours. After the reaction mixture was allowed to cool, a white powder formed was separated by filtering, and washed twice with 5 ml of DMF and 10 ml of ether to give 3.59 g of white crystals of 2,5-dimethoxyxylylenebistriphenylphosphonium chloride (yield 80%).

Under an argon atmosphere, 1.6 g (3 mmol) of the 2,5-dimethoxyxylylenebistriphenylphosphonium chloride was added to and suspended in 15 ml of dry THF, 4 ml of a hexane solution of 15% n-butyllithium was added, and the resultant mixture was stirred for 2 minutes. Then, a solution of 1.45 g (6.25 mmol) of formyltetrathiafulvalene in 15 ml of THF was added, and the mixture was stirred for 4 hours. After the reaction, 50 ml of methanol was added to form a precipitate, and the precipitate was separated by filtering, washed with 50 ml of methanol, washed with water, washed with methanol and dried. The solid obtained was recrystallized from DMF to give 0.53 g of a blackish violet powder of the intended Compound (Im) (yield 28.8 9).

Table 1 summarizes the thermal decomposition temperature Td of Compound (Im), its elemental analysis values, its M/Z in mass spectrometry, its $E_1$ and $\Delta E$ determined by cyclic voltammetry, and its capability of directly forming a complex. As is clear in Table 1, Compound (Im) had a thermal decomposition temperature of as high as 246° C., or was found to be excellent in thermal stability.

Figure 13:
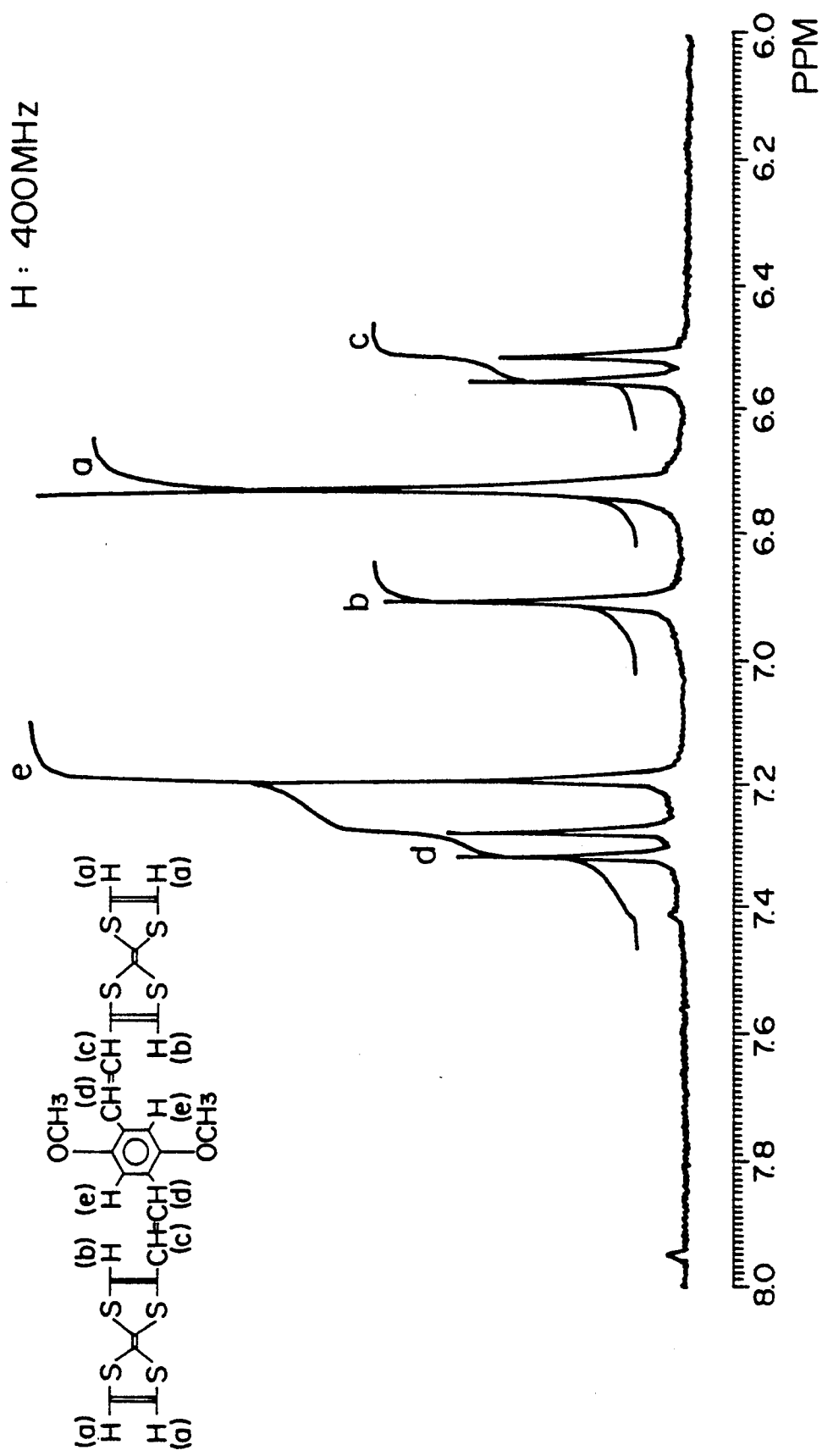
FIG. 13 is an $^1$H-NMR analysis chart of a compound of this invention, obtained in Example 13.

Further, the elemental analysis values, the M/Z in mass spectrometry and $^1$H-NMR shown in FIG. 13 showed that Compound (Im) was 1,4-bis[2-(tetrathiafulvalen-2-yl)vinyl]-2,5-dimethoxybenzene of the following formula.

EXAMPLE 14

Preparation of 1,4-bis[2-(tetrathiafulvalen-2-yl)vinyl]-2,5-dichlorobenzene [compound (In)]

8.75 Grams (50 mmol) of 2.5-dichloro-1,4-xylene, 20.0 g (112 mmol) of N-bromosuccinimide and 0.73 g (3 mmol) of benzoyl peroxide were dissolved in 100 ml of carbon tetrachloride, and the resultant mixture was stirred under heat and refluxed for 6 hours. The reaction liquid was washed with water and dried over Glauber's salt, and the solvent was distilled off to give a white solid. The white solid was recrystallized from ethyl alcohol to give 6.2 g of a white crystal of 2,5-dichloro-1,4-bis(bromomethyl)benzene (yield 37.2%).

4 Grams (12 mmol) of the 2,5-dichloro-1,4-bis(bromomethyl)benzene and 6.6 g (26.4 mmol) of triphenylphosphine were added to 45 ml of DMF, and the resultant mixture was stirred at 130° C. for 3 hours. After the reaction mixture was allowed to cool, a white powder formed was separated by filtering and washed twice with 10 ml of DMF and 20 ml of ether to give 9.9 g (11.6 mmol) of a white crystal of 2,5-dichloroxylyienebistriphenylphosphonium bromide.

Under an argon atmosphere, 2.7 g (3.15 mmol) of the 2,5-dichloroxylylenebistriphenylphosphonium bromide was added to and suspended in 15 ml of dry THF, 4 ml of a hexane solution of 15% n-butyllithium (containing 6.4 mmol of n-butyllithium) was added, and the resultant mixture was stirred for 2 minutes. Then, a solution of 1.45 g (6.25 mmol) of formyltetrathiafulvalene in 15 ml of THF was added, and the resultant mixture was stirred for 3 hours. After the reaction, 60 ml of methanol was added to form a precipitate. The precipitate was separated by filtering, washed with 30 ml of methanol, washed with water, washed with methanol and dried. The so-obtained solid was recrystallized from DMF to give 1.16 g of the intended, blackish violet, Compound (In) (yield 62%).

Table 1 summarizes the thermal decomposition temperature Td of Compound (In), its elemental analysis values, its M/Z in mass spectrometry, its $E_1$ and $\Delta E$ determined by cyclic voltammetry, and its capability of directly forming a complex. As is clear in Table 1, Com-

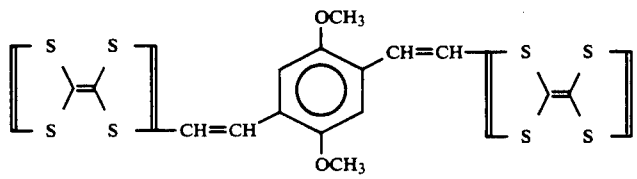

Compound (1m) had $E_1$ of 0.43 V and $\Delta E$ of 0.30 V, or found to be rich in electron donating nature. As is detailed in Example 22 which will be described later, it was also found that Compound (Im) was also capable of forming a complex with an electron acceptor under a direct complex forming method.

pound (In) had a thermal decomposition temperature of as high as 260° C., or was found to be excellent in thermal stability.

Figure 14:
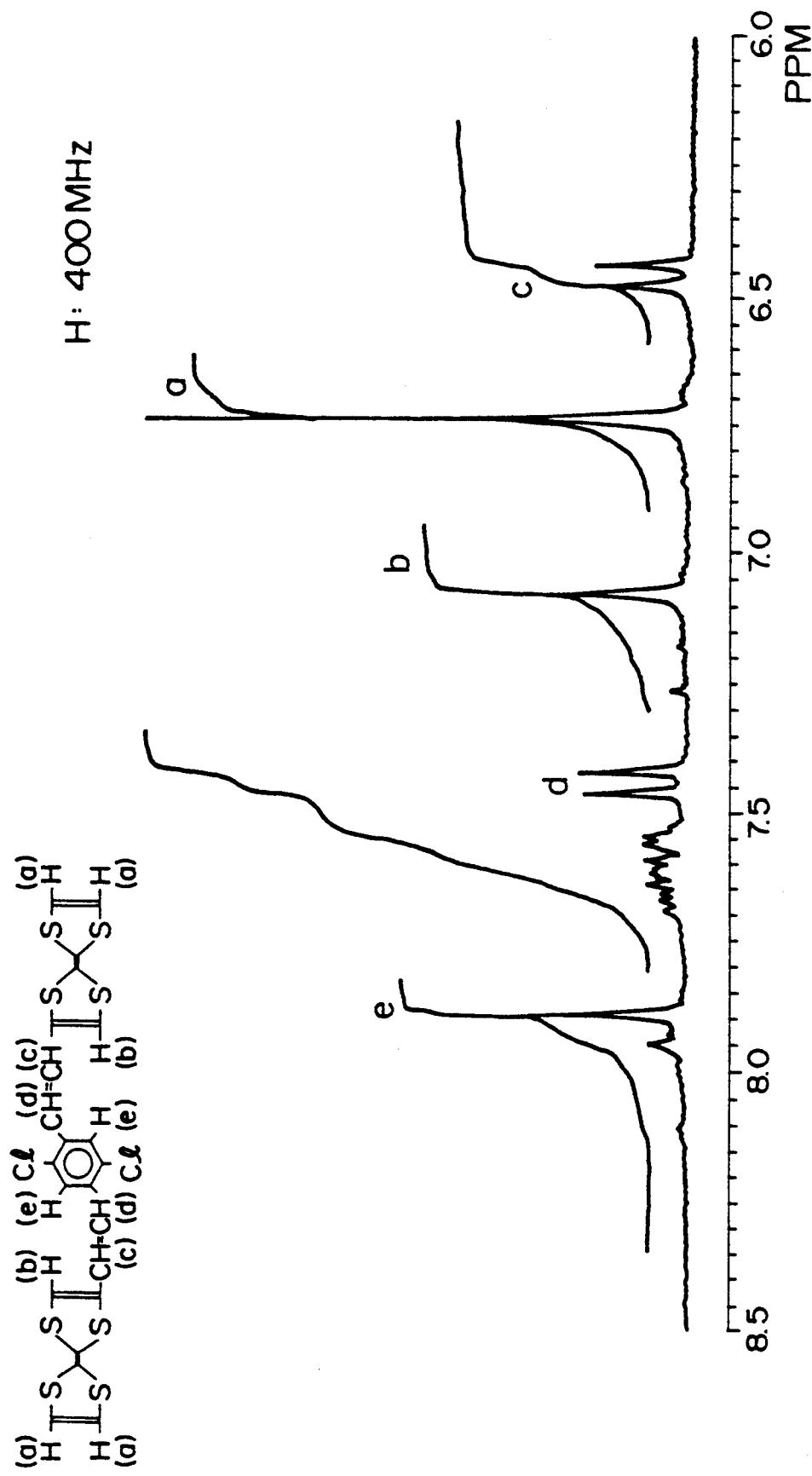
FIG. 14 is an $^1$H-NMR analysis chart of a compound of this invention, obtained in Example 14.

Further, the elemental analysis values, the M/Z in mass spectrometry and $^1$H-NMR shown in FIG. 14 showed that Compound (In) was 1,4-bis[2-(tetrathiafulvalen-2-yl)vinyl]-2,5-dichlorobenzene of the following formula.

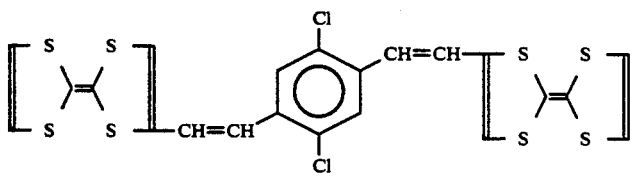

Compound (In) had $E_1$ of 0.47 V and $\Delta E$ of 0.31 V, or found to be rich in electron donating nature. As is detailed in Example 22 which will be described later, it was also found that Compound (In) was also capable of forming a complex with an electron acceptor under a direct complex forming method.

EXAMPLE 15

Preparation of 1,4-bis[2-(tetrathiafulvalen-2-yl)vinyl]-2,3,5,6-tetramethylbenzene [Compound (Io)]

3.0 Grams (10.1 mmol) of 2,3,5,6-tetramethyl-1,4-bis(-bromomethyl)benzene and 5.3 g (20.2 mmol) of triphenylphosphine were added to 50 ml of DMF, and the resultant mixture was stirred at 120° C. for 1 hour. The reaction mixture was allowed to cool, a white powder formed was separated by filtering, washed with dichloromethane and dried. The yield of the resultant 2,3,5,6-tetramethylxylylenebistriphenylphosphonium bromide was 5.35 g (yield 64.6%).

Under an argon atmosphere, 3 g (3.7 mmol) of the 2,3,5,6-tetramethylxylylenebistriphenylphosphonium bromide was added to and suspended in 15 ml of dry THF, 6.5 ml of a hexane solution of 15% n-butyllithium was added, and the resultant mixture was stirred for 2 minutes. Then, a solution of 1.71 g (7.4 mmol) of formyltetrathiafulvalene in 20 ml of THF was added, and the mixture was stirred for 1 hour. After the reaction, 50 ml of methanol was added to form a precipitate. The precipitate was separated by filtering, washed with 50 ml of methanol, washed with water, washed with methanol and dried. The resultant solid was recrystallized from DMF to give 0.4.g of the intended, blackish violet, Compound (Io) (yield 18%).

Table 1 summarizes the thermal decomposition temperature Td of Compound (Io), its elemental analysis values, its M/Z in mass spectrometry, its $E_1$ and $\Delta E$ determined by cyclic voltammetry, and its capability of directly forming a complex. As is clear in Table 1, Compound (Io) had a thermal decomposition temperature of as high as 236° C., or was found to be excellent in thermal stability.

Further, the elemental analysis values and the M/Z in mass spectrometry showed that Compound (Io) was 1,4-bis-[2-(tetrathiafulvalen-2-yl)vinyl]-2,3,5,6-tetramethylbenzene of the following formula.

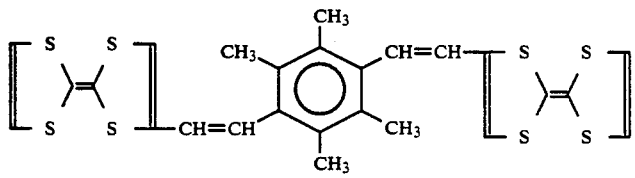

Compound (Io) had $E_1$ of 0.50 V and $\Delta E$ of 0.35 V, or found to be rich in electron donating nature. As is detailed in Example 22 which will be described later, it was also found that Compound (Io) was also capable of forming a complex with an electron acceptor under a direct complex forming method.

EXAMPLE 16

Preparation of 1,4-bis[2-(tetrathiafulvalen-2-yl)vinyl]-2-methylbenzene [Compound (Ip)]

Diethyl 2-methylterephthalonitrile as a starting material was prepared according to a known report (Anzalone, Luigi; Hirsch, Jerry A.; J. Org. Chem., 1985, 50, 2128–2133).

Under an argon atmosphere, a 500 ml round-bottomed flask was charged with 140 ml of a toluene solution of 4.6 g (33 mmol) of the diethyl 2-methylterephthalonitrile, and further, 87 ml of a toluene solution of 18.6 g (131 mmol) of diisobutylaluminum hydride was added dropwise at −78° C. The resultant mixture was stirred for 30 minutes as it was, and then allowed to further react at room temperature for 5 hours. While the reaction mixture was hot, 4 ml of methanol was added to decompose an excess amount of the diisobutylaluminum hydride. Thereafter, the reaction mixture was poured into 250 ml of a saturated ammonium chloride aqueous solution, and the resultant mixture was stirred at room temperature for 20 minutes. The reaction mixture was recharged into a separating funnel, 100 ml of 10% sulfuric acid was added, and the resultant mixture was shaken vigorously. And, an organic layer formed was separated. This organic layer was washed with sodium bicarbonate and salt water, and dried over magnesium sulfate. The solvent was distilled off with a rotary evaporator, and the residue was purified by column chromatography to give 2.8 g (19 mmol) of 2-methylterephthalaldehyde.

A 200 ml round-bottomed flask was charged with 1 g (25 mmol) of lithium aluminum hydride, and under an argon atmosphere, 50 ml of anhydrous tetrahydrofuran was added. While the resultant mixture was stirred, 50 ml of an anhydrous tetrahydrofuran solution of 2.8 g (19 mmol) of 2-methylterephthalaldehyde was added through a dropping funnel over 20 minutes. The resultant mixture was heat-refluxed for 2 hours, and while the reaction mixture was hot, 1 ml of water, 1 ml of a 50% sodium hydroxide aqueous solution and 3 ml of water were consecutively added in this order. A white precipitate formed was separated by filtering, and the tetrahydrofuran solution was dried over magnesium sulfate, followed by distilling the solvent off with a rotary evaporator and drying under reduced pressure, whereby 2.7 g (18 mmol) of 2.5-bis(hydroxymethyl)toluene was obtained (yield 95%).

A 200 ml round-bottomed flask was charged with the entire amount (2.7 g) of the above 2,5-bis(hydroxymethyl)toluene, and 60 ml of dichloromethane was added thereto and suspended therein by stirring the mixture. Added dropwise thereto was 4 ml (5.5 mmol) of thionyl chloride, and the resultant mixture was stirred at room temperature for 3 hours and subjected to extraction by adding 50 ml of water. An organic layer formed was washed with water and with salt water, and the solvent was distilled off. The residue was purified by silica gel column chromatography using 30 g of silica gel to give 2.5 g (13 mmol) of 2,5-bis(chloromethyl)toluene (yield 72%). 2.3 Grams (12 mmol) of this 2,5-bis(chloromethyl)toluene and 6.6 g,(26.4 mmol) of triphenylphosphine were added to 45 ml of DMF, and the resultant mixture was stirred under heat at 130° C. for 2 hours. After the reaction mixture was allowed to cool, a white powder formed was separated by filtering, and washed twice with 10 ml of DMF and 20 ml of ether to give 7.9 g of white crystals of 2-methylxylylenebistriphenylphosphonium chloride (yield 95%).

Under an argon atmosphere, 2.1 g (3 mmol) of the above 2-methylxylylenebistriphenylphosphonium chloride was added to and suspended in 15 ml of dry THF, 4 ml of a hexane solution of 5% n-butyllithium was added, and the resultant mixture was stirred for 2 minutes. Then, a solution of 1.45 g (6.25 mmol) of formyltetrathiafulvalene in 15 ml of THF was added, and the resultant mixture was stirred for 3 hours. After the reaction, 60 ml of methanol was added to form a precipitate, the precipitate was separated by filtering, washed with 30 ml of water, further washed with water, washed with methanol and dried. The resultant solid was recrystallized from DMF to give 1.1 g of the intended, blackish violet. Compound (Ip) (yield 60%).

Table 1 summarizes the thermal decomposition temperature Td of Compound (Ip), its elemental analysis values, its M/Z in mass spectrometry, its $E_1$ and $\Delta E$ determined by cyclic voltammetry, and its capability of directly forming a complex. As is clear in Table 1, Compound (Ip) had a thermal decomposition temperature of as high as 242° C., or was found to be excellent in thermal stability.

Further, the elemental analysis values and the M/Z in mass spectrometry showed that Compound (Ip) was 1,4-bis-[2-(tetrathiafulvalen-2-yl)vinyl]-2-methylbenzene of the following formula.

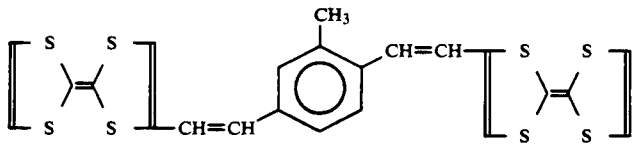

Compound (Ip) had $E_1$ of 0.47 V and $\Delta E$ of 0.26 V, or found to be rich in electron donating nature. As is detailed in Example 22 which will be described later, it was also found that Compound (Ip) was also capable of forming a complex with an electron acceptor under a direct complex forming method.

EXAMPLE 17

Preparation of 1,4-bis[2-[tetrathiafulvalen-2-yl)vinyl]-2.5-dihydroxybenzene [compound (Iq)]

A 100 ml round-bottomed flask was charged with 0.6 g (1 mmol) of 1,4-bis[2-(tetrathiafulvalen-2-yl)vinyl]-2,5-dimethoxybenzene prepared in the method of Example 13, and the atmosphere inside the flask was changed to an argon atmosphere. The flask was further charged with 50 ml of anhydrous dimethyl sulfoxide, and the resultant mixture was stirred under heat in an oil bath at 50° C. to form a solution. With a syringe, 0.4 ml (3 mmol) of trimethylsilyl iodide was added dropwise, and the resultant mixture was directly stirred under heat at 50° C. for 24 hours. The reaction mixture was cooled, 10 ml of methanol was added, and the reaction mixture was stirred at room temperature for 24 hours. The reaction mixture was concentrated by distillation under reduced pressure, 30 ml of methanol was added to form a suspension, and a solid portion was separated by filtering, washed twice with 10 ml of methanol, and recrystallized from N,N-dimethylformamide to give 0.11 g of the intended Compound (Iq) (yield 20%).

Table 1 summarizes the thermal decomposition temperature Td-of Compound (Iq), its elemental analysis values, its M/Z in mass spectrometry, its $E_1$ and $\Delta E$ determined by cyclic voltammetry, and its capability of directly forming a complex. As is clear in Table 1, Compound (Iq) had a thermal decomposition temperature of as high as 270° C., or was found to be excellent in thermal stability.

Further, the elemental analysis values and the M/Z in mass spectrometry showed that Compound (Iq) was 1,4-bis-[2-(tetrathiafulvalen-2-yl)vinyl]-2,5-dihydroxybenzene of the following formula.

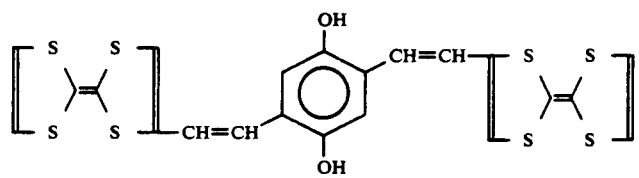

Compound (Iq) had $E_1$ of 0.46 V and $\Delta E$ of 0.30 V, or found to be rich in electron donating nature. As is detailed in Example 22 which will be described later, it was also found that Compound (Iq) was also capable of forming a complex with an electron acceptor under a direct complex forming method.

EXAMPLE 18

Preparation of 1,4-bis[2-(1,4-dithia-5,8-selenafulvalen-2-yl)vinyl]-2,5-dimethylbenzene [compound (Ir)]

7 Grams (39.8 mmol) of methyl 1,3-dithiol-2-one-4-carboxylate and 6.2 g (48.4 mmol) of triphenylphosphine were refluxed and dissolved in 50 ml of benzene. Added dropwise thereto was 150 ml of a benzene solution of 5.8 g (21.1 mmol) of 1,3-diselenol-2-selenone under an argon current over 1 hour. After the addition, the resultant mixture was refluxed for 20 minutes, and the solvent was distilled off, followed by separation and purification by column chromatography, whereby 1.3 g (3.65 mmol) of methyl 1,4-dithia-5,8-diselenafulvalen-2-carboxylate was obtained (yield 9.2%).

4.9 Grams of a toluene solution of 70% sodium bis(2-methoxyethoxy)aluminum hydride (SMEAH) (containing 17.1 mmol of SMEAH) was dissolved in 6 ml of anhydrous toluene, and the resultant mixture was cooled to 0° C. under an argon gas current. A solution of 1.6 g (18.4 mmol) of anhydrous morpholin (MPL) in anhydrous toluene was slowly added dropwise thereto over 30 minutes to prepare an SMEAH-MPL mixed reagent.

1.2 Grams (3.4 mmol) of the methyl 1,4-dithia-5,8-diselenafulvalene-2-carboxylate was dissolved in 120 ml of anhydrous toluene, and the resultant mixture was cooled to 0° C. The above-prepared SMEAH-MPL mixed reagent was slowly added dropwise under an argon gas current over 30 minutes. After the addition, the mixture was stirred at 0° C. for 30 minutes, and while the resultant solution was at 0° C., 2N sulfuric acid was added to acidify the solution. Anhydrous magnesium sulfate was added to solidify the water phase thereof, the solidified water phase was separated by filtering, and the remaining solid was washed with dichloromethane. These two liquids (filtrate and the dichloromethane wash liquid) were together concentrated, and purified by column chromatography to give 0.5 g (1.5 mmol) of 1,4-dithia-5,8-diselena-2-formylfulvalene (yield 45%).

0.55 Gram (0.75 mmol) of 2,5-dimethylxylyienebistriphenylphosphonium chloride was suspended in 20 ml of anhydrous THF, and at room temperature under an argon gas current, 2.0 ml of a hexane solution of 15% n-butyllithium (containing 3.2 mmol of n-butyllithium) was added. After the resultant mixture was stirred at room temperature for 5 minutes, a solution of 0.5 g (1.5 mmol) of the 1,4-dithia-5,8-diselena-2-formylfulvalene in 20 ml of anhydrous THF was added, and the mixture was stirred at room temperature for 2 hours. An equal amount of methanol was added to terminate the reaction, and a solid formed was separated by filtering, washed with methanol, and recrystallized from DMF to give 280 mg of golden plate-like crystals of the intended Compound (Ir) (yield 25%).

Table 1 summarizes the thermal decomposition temperature Td of Compound (Ir), its elemental analysis values, its M/Z in mass spectrometry, its $E_1$ and $\Delta E$ determined by cyclic voltammetry, and its capability of directly forming a complex. As is clear in Table 1, Compound (Ir) had a thermal decomposition temperature of as high as 248° C., or was found to be excellent in thermal stability.

Further, the elemental analysis values and the M/Z in mass spectrometry showed that Compound (Ir) was 1,4-bis-[2-(1,4-dithia-5,8-diselenafulvalen-2-yl)vinyl]-2,5-dimethylbenzene of the following formula.

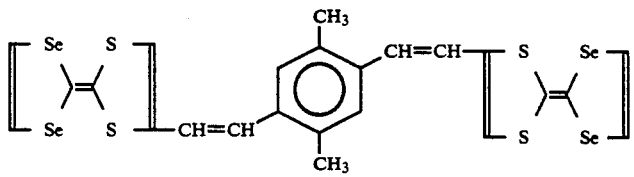

Compound (Ir) had $E_1$ of 0.53 V and $\Delta E$ of 0.22 V, or found to be rich in electron donating nature. As is detailed in Example 22 which will be described later, it was also found that Compound (Ir) was also capable of forming a complex with an electron acceptor under a direct complex forming method.

EXAMPLE 19

Preparation of 1,4-bis[2-(1,4-diselena-5,8-dithiafulvalen-2-yl)vinyl]-2,5-dimethylbenzene [compound (Is)]

Figure 15:
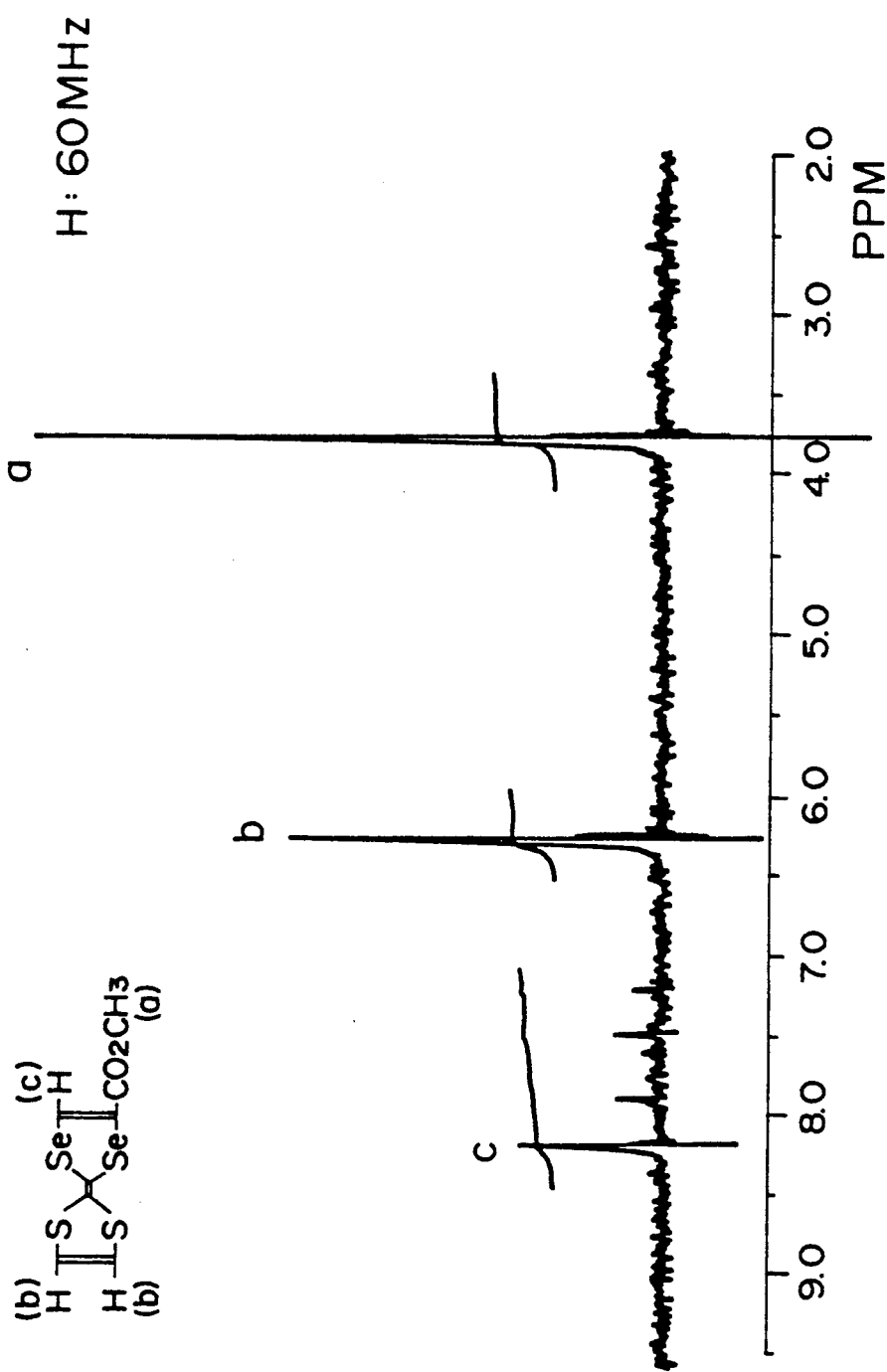
FIG. 15 is an $^1$H-NMR analysis chart of a compound of this invention, obtained in Example 18.

19 Grams (161 mmol) of 1,3-dithiol-2-one and 31 g (242 mmol) of triphenylphosphine were refluxed and dissolved in 200 ml of benzene. Added dropwise thereto was a solution of 31 g (81 mmol) of dimethyl 1,3-diselenol-2-selenone-4,5-dicarboxylate in 400 ml of benzene under an argon gas current over 3 hours. After the addition, the resultant mixture was refluxed, followed by distillation of the solvent off and separation and purification by column chromatography, whereby 2.5 g (6.0 mmol),of dimethyl 1,4-diselena-5,8-dithia-2,3-dicarboxylate was obtained (yield 7.5%). This compound had a melting point of 115.5° C., and the $^1$H-NMR chart thereof is as shown in FIG. 15. 2 Grams (4.8 mmol) of this dimethyl 1.4-diselena-5,8-dithia-2.3-dicarboxylate was dissolved in 20 ml of hexamethylphosphoricamide, 1 g (9.5 mmol) of LiBr·H$_2$O was added, and the resultant mixture was stirred for 1 hour. Added thereto was 300 ml of water, and the resultant mixture was subjected to extraction with dichloromethane, and an organic phase formed was washed with water, followed by concentration and purification by column chromatography, whereby 0.6 g (1.68 mmol) of methyl 1,4-diselena-5,8-dithia-2-carboxylate (melting point 94.0° C.) was obtained (yield 35%). 0.5 Gram (1.4 mmol) of this product was weighed out and dissolved in 120 ml of anhydrous toluene, and the resultant mixture was cooled to 0° C. The same SMEAH-MPL reagent as that prepared in Example 18 was slowly added dropwise under an argon gas current over 30 minutes. After the addition, the resultant mixture was stirred at 0° C. for 30 minutes, and while the resultant solution was at 0° C., 2N sulfuric acid was added to acidify the solution. Anhydrous magnesium sulfate was added to solidify the water phase thereof and remove it by filtering, the remaining solid was washed with dichloromethane, and these two liquids (filtrate and the dichloromethane wash liquid) were together concentrated and purified by column chromatography to give 0.3 g (0.9 mmol) of 1,4-diselena-5,8-dithia-2-formylfulvalene.

0.33 Gram (0.45 mmol) of 2,5-dimethylxylylenebistriphenylphosphonium chloride was suspended in 20 ml of anhydrous THF, and at room temperature under an argon gas current, 1.0 ml of a hexane solution of 15% n-butyllithium (containing 1.6 mmol of n-butyllithium) was added. The resultant mixture was stirred at room temperature for 5 minutes, a solution of 0.3 g (0.9 mmol) of the 1,4-diselena-5,8-dithia-2-formylfulvalene in 10 ml of anhydrous THF was added, and the resultant mixture was stirred at room temperature for 2 hours. An equal amount o? methanol was added to terminate the reaction, and a solid formed was separated by filtering, washed with methanol, and recrystallized from DMF to give 150 mg of golden plate-like crystals of the intended Compound (Is) (yield 25%).

Table 1 summarizes the thermal decomposition temperature Td of Compound (Is), its elemental analysis values, its M/Z in mass spectrometry, its $E_1$ and $\Delta E$ determined by cyclic voltammetry, and its capability of directly forming a complex. As is clear in Table 1, Compound (Is) had a thermal decomposition temperature of as high as 235° C., or was found to be excellent in thermal stability.

Further, the elemental analysis values and the M/Z in mass spectrometry showed that Compound (Is) was 1,4-bis-[2-(1,4-diselena-5,8-dithiafulvalen-2-yl)vinyl]-2,5-dimethylbenzene of the following formula.

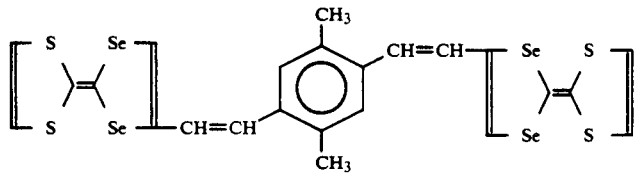

Compound (Is) had $E_1$ of 0.52 V and $\Delta E$ of 0.23 V, or found to be rich in electron donating nature. As is detailed in Example 22 which will be described later, it was also found that Compound (Is) was also capable of forming a complex with an electron acceptor under a direct complex forming method.

EXAMPLE 20

Preparation of 1,4-bis[2-(tetraselenafulvalen-2-yl)vinyl]-2,5-dichlorobenzene [Compound (It)]

Under an argon atmosphere, 2.7 g (3.2 mmol) of 2,5-dichloroxylylenebistriphenylphosphonium bromide was added to and suspended in 15 ml of dry THF, 4 ml of a hexane solution of 15% n-butyllithium was added, and the resultant mixture was stirred for 2 minutes. Then, a solution of 2.6 g (6.25 mmol) of formyltetraselenafulvalene in 15 ml of THF was added, and the mixture was stirred for 3 hours. After the reaction, 60 ml of methanol was added to form a precipitate. The precipitate was separated by filtering, followed by washing with 30 ml of methanol, washing with water, washing with methanol and drying. The resultant product was recrystallized from DMF to give 1.6 g of the intended, blackish violet, Compound (It) (yield 25%).

Table 1 summarizes the thermal decomposition temperature Td of Compound (It), its elemental analysis values, its M/Z in mass spectrometry, its $E_1$ and $\Delta E$ determined by cyclic voltammetry, and its capability of directly forming a complex. As is clear in Table 1, Compound (It) had a thermal decomposition temperature of as high as 245° C., or was found to be excellent in thermal stability.

Further, the elemental analysis values and the M/Z in mass spectrometry showed that Compound (It) was 1,4-bis-[2-(tetraselenafulvalen-2-yl)vinyl]-2,5-dichlorobenzene of the following formula.

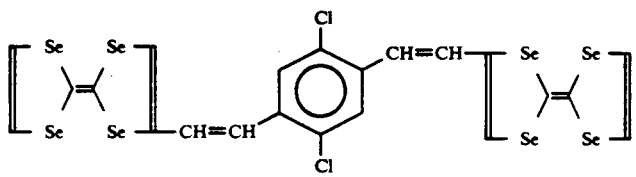

Compound (It) had $E_1$ of 0.50 V and $\Delta E$ of 0.20 V, or found to be rich in electron donating nature. As is detailed in Example 22 which will be described later, it was also found that Compound (It) was also capable of forming a complex with an electron acceptor under a direct complex forming method.

EXAMPLE 21

Preparation of 1.4-bis[4,5,8-trithia-1-selenafulvalen-2-yl)vinyl]-2,5-dimethylbenzene [Compound I(u)]

2.8 Grams (20.8 mmol) of 1,3-dithiol-2-thione and 8 g (30.5 mmol) of triphenylphosphine were dissolved in 30 ml of benzene and the resultant mixture was refluxed. A solution of 4 g (10.2 mmol) of dimethyl 1,3-diselenol-2-selenone-4,5-dicarboxylate in 200 ml of benzene was slowly added dropwise thereto under an argon gas current over 2 hours. After the addition, the resultant mixture was further refluxed for 30 minutes, and the solvent was distilled off, followed by purification by column chromatography, whereby 1.6 g (4.36 mmol) of grayish brown dimethyl 4,5,8-trithia-1-selenafulvalene-2,3-dicarboxylate (melting point 114.1° C.) was obtained (yield 43%). The total amount of this product was dissolved in 8 ml of HMPA, 0.9 g (8.6 mmol) of LiBr·H₂O was added, and the resultant mixture was stirred at 80° C. for 1 hour. Added thereto was 100 ml of water, the resultant mixture was subjected to extraction with dichloromethane, and an organic layer formed was washed with water, concentrated and purified by column chromatography to give 1.2 g (3.9 mmol) of a orange solid (melting point 112.9° C.) of methyl 4,5,8-trithia-1-selenafulvalene-2-carboxylate (yield 89%).

Figure 16:
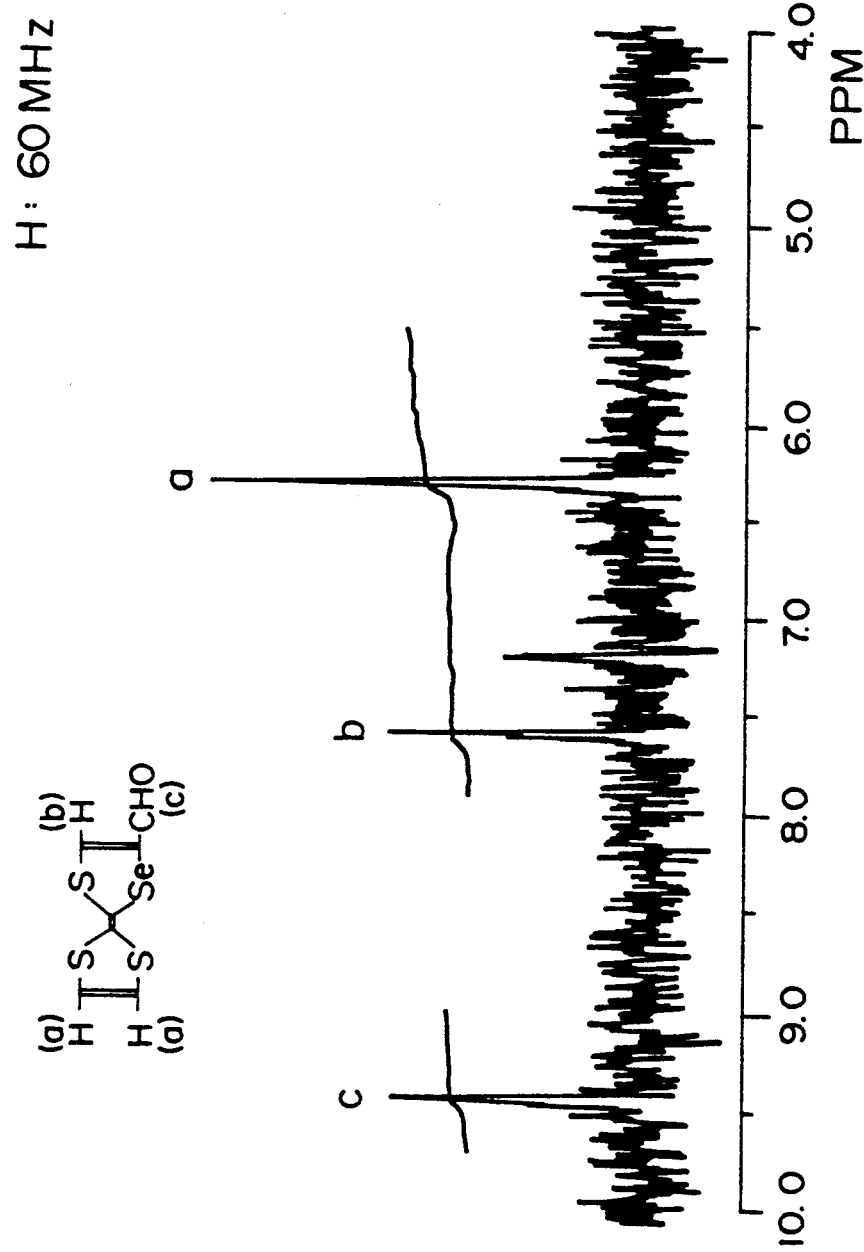
FIG. 16 is an $^1$H-NMR analysis chart of an intermediate compound in Example 21.

4.1 Milliliters of a toluene solution containing 14 mmol of sodium bis(2-methoxyethoxy)aluminum hydride (SMEAH) was dissolved in 4 ml of anhydrous toluene, and the resultant mixture was cooled to 0° C. Added dropwise thereto was 4 ml of a toluene solution of 1.3 g (14.9 mmol) of anhydrous morpholine (MPL) under an argon gas current over 10 minutes to prepare an SMEAH-MPL mixed reagent. 1.7 Grams (5.5 mmol) of the methyl 4,5,8-trithia-1-selenafulvalene-2-carboxylate was dissolved in 40 ml of anhydrous toluene, and the resultant mixture was cooled to −10° C. The above-prepared SMEAH-MPL mixed reagent was slowly added dropwise thereto under an argon gas current over 30 minutes. After the addition, the resultant solution was stirred for 30 minutes, 2N sulfuric acid was added to convert the solution to weakly acidic, and then, sodium sulfate was added to solidify the aqueous phase thereof. The remaining organic layer was recovered by filtering, and the sodium sulfate was washed with dichloromethane. The organic phases obtained were together concentrated and purified by column chromatography to give 0.27 g (0.825 mmol) of 4,5,8-trithia-1-selena-2-formylfulvalene (yield 15%). This compound had a melting point of 116.8° C. and a decomposition temperature of 189° C., and the $^1$H-NMR chart thereof is as shown in FIG. 16.

0.28 Gram (0.39 mmol) of 2,5-dimethylxylylenebistriphenylphosphonium chloride was suspended in 20 ml of anhydrous THF, and at room temperature under an argon gas current, 0.5 ml of a hexane solution of 5% n-butyllithium (containing 0.8 mmol of n-butyllithium) was added. The color of the resultant solution was changed from white to reddish brown, which showed ylide formation. After the solution was stirred at room temperature for 10 minutes, a solution of 0.25 g (0.8 mmol) of the 4,5,8-trithia-1-selena-2-formylfulvalene in 20 ml of THF was added, and the resultant mixture was stirred at room temperature for 2 hours. An equal amount of methanol was added to terminate the reaction, and a solid formed was separated by filtering, followed by washing with methanol and recrystallization from DMF, whereby 10 mg of brown plate-like crystals of the intended Compound (Iu) was obtained (yield 27%).

Table 1 summarizes the thermal decomposition temperature Td of Compound (Iu), its elemental analysis values, its M/Z in mass spectrometry, its $E_1$ and $\Delta E$ determined by cyclic voltammetry, and its capability of directly forming a complex. As is clear in Table 1, Compound (Iu) had a thermal decomposition temperature of as high as 235° C., or was found to be excellent in thermal stability.

Further, the elemental analysis values, the M/Z in mass spectrometry and the $^1$H-NMR results shown in FIG. 17 showed that Compound (Iu) was 1,4-bis-[2-(4,5,8-trithia-1-selenafulvalen-2-yl)vinyl]-2,5-dimethylbenzene of the following formula.

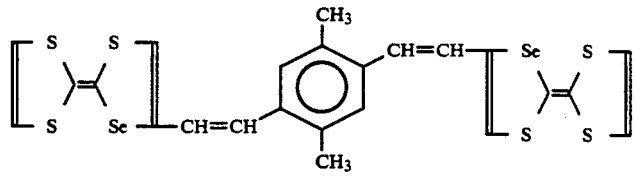

Compound (Iu) had $E_1$ of 0.53 V and $\Delta E$ of 0.20 V, or found to be rich in electron donating nature. As is detailed in Example 22 which will be described later, it was also found that Compound (Iu) was also capable of forming a complex with an electron acceptor under a direct complex forming method.

COMPARATIVE EXAMPLE 1

The following three known electron-donating compounds (a), (b) and (c) were measured for a melting point, $E_1$ and $\Delta E$, and examined with regard to the capability of directly forming a complex.

(a) Bisethylenedithiotetrathiafulvalene (BEDTTTF)

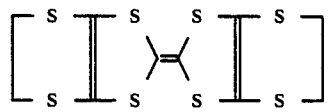

(b) Tetramethyltetrathiafulvalene (TMTTF)

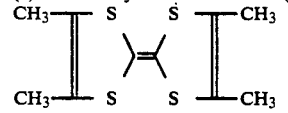

(c) Tetrathiafulvalene (TTF)

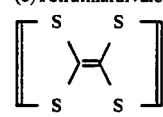

measurements. Table 1 shows that the known compounds (a) BEDTTTF and (b) TMTTF are inferior in electron donating nature since these compounds had $E_1$ of as high as 1.0 V and 0.86 V and $\Delta E$ of as great as 0.44 and 0.53 respectively. As is shown in Comparative Examples 2 and 3 to be described later, therefore, these compounds were incapable of directly forming a complex. It was also shown that the known compound (c) TTF was inferior in electron donating nature since it had $E_1$ of as high as 0.85 V and $\Delta E$ of as great as 0.41 V, and that it was poor in thermal stability since it had a melting point of as low as 115 to 119° C.

TABLE 1

| No. | Compound of general formula (I) | Thermal decomposition temperature Td (°C.) | | Elemental analysis value | | | | | |
|---|---|---|---|---|---|---|---|---|---|
| | | | | C | H | O | S | Se | Cl |
| Ex. 1 | Compound (Ia) | 225 | Calculated | 49.4 | 2.6 | | 47.9 | | |
| | | | Found | 49.5 | 2.7 | | 47.8 | | |
| Ex. 2 | Compound (Ib) | 270 | Calculated | 51.2 | 3.2 | | 45.5 | | |
| | | | Found | 51.4 | 3.3 | | 45.3 | | |
| Ex. 3 | Compound (Ic) | 230 | Calculated | 30.7 | 1.9 | | | 67.4 | |
| | | | Found | 30.6 | 2.0 | | | 67.0 | |
| Ex. 4 | Compound | 245 | Calculated | 33.8 | 2.6 | | | 63.6 | |

TABLE 1-continued

|  |  |  |  |  |  |  |  |  |
|---|---|---|---|---|---|---|---|---|
|  | (Id) |  | Found | 34.0 | 2.7 |  | 63.2 |  |
| Ex. 5 | Compound | 227 | Calculated | 45.3 | 3.0 |  | 51.8 |  |
|  | (Ie) |  | Found | 45.2 | 3.2 |  | 51.4 |  |
| Ex. 6 | Compound | 236 | Calculated | 45.0 | 3.5 |  | 51.5 |  |
|  | (If) |  | Found | 45.0 | 3.6 |  | 51.4 |  |
| Ex. 7 | Compound | 220 | Calculated | 48.9 | 2.8 | 2.8 | 45.8 |  |
|  | (Ig) |  | Found | 49.1 | 3.0 | 3.1 | 44.8 |  |
| Ex. 8 | Compound | 248 | Calculated | 46.4 | 2.3 |  | 45.0 | 6.2 |
|  | (Ih) |  | Found | 46.5 | 2.3 |  | 44.8 | 6.2 |
| Ex. 9 | Compound | 270 | Calculated | 54.4 | 4.2 |  | 41.4 |  |
|  | (Ii) |  | Found | 54.5 | 4.2 |  | 41.3 |  |
| Ex. 10 | Compound | 215 | Calculated | 47.0 | 2.8 |  | 50.1 |  |
|  | (Ij) |  | Found | 46.9 | 2.9 |  | 49.8 |  |
| Ex. 11 | Compound | 210 | Calculated | 47.9 | 3.1 |  | 49.1 |  |
|  | (Ik) |  | Found | 48.0 | 3.1 |  | 49.0 |  |
| Ex. 12 | Compound | 242 | Calculated | 38.4 | 2.4 |  | 17.1 | 42.1 |
|  | (Il) |  | Found | 38.6 | 2.4 |  | 16.9 | 42.0 |
| Ex. 13 | Compound | 246 | Calculated | 48.5 | 3.0 | 5.4 | 43.1 |  |
|  | (Im) |  | Found | 48.4 | 3.0 | 5.3 | 43.3 |  |
| Ex. 14 | Compound | 260 | Calculated | 43.8 | 2.0 |  | 42.4 | 11.8 |
|  | (In) |  | Found | 43.6 | 2.1 |  | 42.0 | 12.3 |
| Ex. 15 | Compound | 236 | Calculated | 52.0 | 5.3 |  | 42.7 |  |
|  | (Io) |  | Found | 51.9 | 5.3 |  | 42.8 |  |
| Ex. 16 | Compound | 242 | Calculated | 50.4 | 2.9 |  | 46.7 |  |
|  | (Ip) |  | Found | 50.8 | 2.9 |  | 46.3 |  |
| Ex. 17 | Compound | 270 | Calculated | 46.6 | 2.5 | 5.7 | 45.2 |  |
|  | (Iq) |  | Found | 46.8 | 2.5 | 5.9 | 44.8 |  |
| Ex. 18 | Compound | 248 | Calculated | 38.4 | 2.4 |  | 17.1 | 42.1 |
|  | (Ir) |  | Found | 38.6 | 2.4 |  | 16.9 | 42.1 |
| Ex. 19 | Compound | 232 | Calculated | 38.4 | 2.4 |  | 17.1 | 42.1 |
|  | (Is) |  | Found | 38.7 | 2.3 |  | 17.2 | 41.8 |
| Ex. 20 | Compound | 245 | Calculated | 27.0 | 1.2 |  | 64.6 | 7.2 |
|  | (It) |  | Found | 27.2 | 1.2 |  | 64.0 | 7.6 |
| Ex. 21 | Compound | 235 | Calculated | 43.1 | 2.7 |  | 29.3 | 24.1 |
|  | (Iu) |  | Found | 42.8 | 2.6 |  | 29.8 | 24.8 |
| Comp. Ex. 1 | Known compound (a) BEDTTTF | mp. 246–247 |  | not measured |  |  |  |  |
|  | Known compound (b) TMTTF | mp. 244–245 |  | not measured |  |  |  |  |
|  | Known compound (c) TTF | mp. 115–119 |  | not measured |  |  |  |  |

| No. | Compound of general formula (I) | M/Z | E1 (V) | ΔE (V) | Capability of directly forming complex |
|---|---|---|---|---|---|
| Ex. 1 | Compound (Ia) | 534 | 0.49 | 0.31 | possible (O) |
| Ex. 2 | Compound (Ib) | 562 | 0.47 | 0.23 | O |
| Ex. 3 | Compound (Ic) | 937 | 0.57 | 0.20 | O |
| Ex. 4 | Compound (Id) | 993 | 0.53 | 0.30 | O |
| Ex. 5 | Compound (Ie) | 742 | 0.55 | 0.26 | O |
| Ex. 6 | Compound (If) | 746 | 0.52 | 0.32 | O |
| Ex. 7 | Compound (Ig) | 564 | 0.46 | 0.31 | O |
| Ex. 8 | Compound (Ih) | 568.5 | 0.49 | 0.31 | O |
| Ex. 9 | Compound (Ii) | 618 | 0.48 | 0.32 | O |
| Ex. 10 | Compound (Ij) | 638 | 0.50 | 0.28 | O |
| Ex. 11 | Compound (Ik) | 652 | 0.52 | 0.30 | O |
| Ex. 12 | Compound (Il) | 750 | 0.53 | 0.28 | O |
| Ex. 13 | Compound (Im) | 594 | 0.43 | 0.30 | O |
| Ex. 14 | Compound (In) | 603 | 0.47 | 0.31 | O |
| Ex. 15 | Compound (Io) | 600 | 0.50 | 0.35 | O |
| Ex. 16 | Compound (Ip) | 548 | 0.47 | 0.26 | O |
| Ex. 17 | Compound (Iq) | 566 | 0.46 | 0.30 | O |
| Ex. 18 | Compound (Ir) | 750 | 0.53 | 0.22 | O |
| Ex. 19 | Compound (Is) | 750 | 0.52 | 0.23 | O |
| Ex. 20 | Compound (It) | 979 | 0.50 | 0.20 | O |
| Ex. 21 | Compound (Iu) | 656 | 0.53 | 0.20 | O |
| Comp. Ex. 1 | Known compound (a) BEDTTTF | not measured | 1.0 | 0.44 | impossible (X) |
|  | Known compound (b) TMTTF | not measured | 0.86 | 0.53 | X |
|  | Known compound (c) TTF | not measured | 0.85 | 0.41 | O |

PREPARATION EXAMPLE OF COMPLEX

EXAMPLE 22

After a flask was charged with 30 mg of the 1,4-bis[2-(tetrathiafulvalen-2-yl)vinyl]benzene [Compound (Ia)] obtained in Example 1, 100 ml of chlorobenzene was added, and the resultant mixture was heated to 120° C. to form a solution. The solution was mixed with 500 mg of tetra-n-butylammonium triiodide, and the resultant mixture was stirred for 5 minutes. The reaction product obtained was recovered by filtering, washed with dichloromethane and dried to give a complex consisting of Compound (Ia) as an electron donor and $I_3$ as an electron acceptor.

Complexes each consisting one of Compounds (Ib) to (Iu) as an electron donor and $I_3$ as an electron acceptor were prepared in the same manner as above.

As described above it has been found that complexes can be obtained by only mixing Compounds (Ia) to (Iu) obtained in Examples 1 to 21 with an electron acceptor.

These twenty-one complexes were (1) measured for identification, (2) subjected to elemental analysis with regard to an electron acceptor, (3) measured for an electron donor/electron acceptor molar ratio (D/A) and (4) measured for electrical conductivity.

In addition, the above measurements (1), (3) and (4) were carried out in the following manner.

(1) Identification of complex

The identification of complexes was conducted by examining the degree of electrical conductivity and identifying an electron acceptor by means of ICP (inductive coupling plasma emission spectral analyzer), an X-ray microanalyzer or voltammetry.

(3) Measurement of D/A

Complexes were aggregates of microcrystallites, and D/A as an average was determined on the basis of the following equation.

$$D/A = \frac{100 \times a \times (r - w/100)}{d \times w}$$

in which:
d: molecular weight of electron donor
a: molecular weight of electron acceptor
w: weight ratio of atom measured (%), and
r: atomic ratio measured in electron acceptor.

(4) Measurement of electrical conductivity

In the case of acicular crystals, lead wires were connected to a complex with a gold paste, and the complex was measured according to a conventional four point probe method. In the case of a powder sample, the powder was charged into a glass cell having a diameter of 1 Mm and pressure-molded at a cylinder pressure of about 130 kg/cm² to form a column having a length of about I to 3 Mm and a diameter of 1 mm, and the column was used as a sample for the measurement. Electrodes were attached to the sample with a gold paste, and the sample was measured for electrical conductivity according to a four point probe method.

Table 2 summarizes the results of these measurements. Table 2 shows that bach complex consisting of one of Compounds (Ia) to (Iu) obtained in Examples 1 to 21 as an electron donor and $I_3$ as an electron acceptor has electrical conductivity. In particular, the complex consisting of Compound (Ic) obtained in Example 3 as an electron donor and $I_3$ as an electron acceptor and the complex consisting of Compound (Ir) obtained in Example IS as an electron donor and $I_3$ as an electron acceptor exhibited electrical conductivity of as high as 200 S/cm.

EXAMPLE 23

A flask was charged with 50 mg of 1,4-bis(2-(tetrathiafulvalen-2-yl)vinyl]-2,5-dimethylbenzene [Compound (Ib)] obtained in Example 2, and 500 mg of iodine was added. The resultant mixture was allowed to stand at room temperature for 3 days. Then, the reaction mixture was taken out, washed and dried to give a complex. Table 2 shows the results of analysis of the complex obtained by this direct complex-forming method. Table 2 shows that this complex had electrical conductivity.

EXAMPLE 24

After a flask was charged with 30 mg of 1,4-bis[2-(tetrathiafulvalen-2-yl)vinyl]benzene (Compound (Ia)] obtained in Example 1, 100 mg of xylene was added, and the resultant mixture was heated to 120° C. to form a solution. The solution was mixed with 500 mg of tetra-n-butylammonium trichloride, and the mixture was stirred for 5 minutes. The reaction product was filtered, washed with dichloromethane, and dried to give a complex. Table 2 shows the results of analysis of the complex obtained by this direct complex-forming method. Table 2 shows that this complex had electrical conductivity.

EXAMPLE 25

A flask was charged with 30 mg of 1,4-bis(2-(tetrathiafulvalen-2-yl)vinyl]-2,5-dimethylbenzene [Compound (Ib)] obtained in Example 2, and 100 mg of xylene was added. The resultant mixture was heated to 120° C. to form a solution. The solution was mixed with 500 mg of tetra-n-butylammonium trichloride, and the mixture was stirred for 5 minutes. The reaction product was filtered, washed with dichloromethane, and dried to give a complex. Table 2 shows the results of analysis of the complex obtained by this direct complex-forming method. Table 2 shows that this complex had electrical conductivity.

EXAMPLE 26

A flask was charged with 30 mg of 1,4-bis(2-(6,7-ethylenedithiotetrathiafulvalen-2-yl)vinyl]-2,5-dimethylbenzene [Compound (Ie)] obtained in Example 5, and 100 ml of chlorobenzene was added. The resultant mixture was heated to 120° C. to form a solution. The solution was mixed with 200 mg of tetra-n-butylammonium bromodiiodide, and the mixture was stirred for 5 minutes. The reaction mixture was slowly cooled to room temperature, and the reaction product was recovered by filtering, washed with dichloromethane, and dried to give a complex. Table 2 shows the results of analysis of the complex obtained by this direct complex-forming method. Table 2 shows that this complex had electrical conductivity.

COMPARATIVE EXAMPLE 2

A flask was charged with 15 mg of bisethylenedithiotetrathiafulvalene (BEDTTTF), and another flask was charged with 15 mg of tetramethyltetrathiafulvalene (TMTTF). Then, 100 mg of chlorobenzene was charged to each of the flasks, and the resultant mixtures were heated to 120° C. to form solutions. Each of the solutions was mixed with 300 mg of tetra-n-butylammonium trichloride, and the resultant mixtures were stirred for 5 minutes. It has been found that none of the BEDTTTF and TYITTF do not form any complex under a direct complex-forming method.

COMPARATIVE EXAMPLE 3

A flask was charged with 15 mg of tetrathiafulvalene (TTF), and 100 mg of chlorobenzene was added. Then the resultant mixture was heated to 120° C. to form a solution. The solution was mixed with 300 mg of tetra-n-butylammonium trichloride, and the resultant mixture was stirred for 5 minutes to form a complex. The electrical conductivity of the complex was 50 S/cm. The results of X-ray diffractometry thereof showed that the-electron donor was converted to I instead of $I_3$, and it is considered that the complex was formed in a different process from those of the above Examples.

tained showed that complexes were formed of crystals in various ratios. Table 3 shows the data.

TABLE 3

| Example No. for preparation of complex | Example No. for Preparation of electron donor | Electron donor (D) | Electron acceptor (A) | | Peak height ratio in X-ray microanalyzer S:I | *1 Corrected S:I | D/A |
|---|---|---|---|---|---|---|---|
| 22 | 2 | Compound (Ib) | $I_3$ | Acicular | 10:4.3 | 8:3.1 | 0.97 |
| | | | | Column | 10:2.9 | 8:2.1 | 1.43 |
| 22 | 5 | Compound (Ie) | $I_3$ | Acicular | 10:2.0 | 12:2.2 | 1.36 |
| | | | | Column | 10:1.3 | 12:1.4 | 2.14 |
| 26 | 5 | Compound (Ie) | $I_2Br$ | Acicular | 10:2.1 | 12:2.3 | 0.87 |
| | | | | Column | 10:1.0 | 12:1.1 | 1.82 |

*1: Corrected on the basis of S and I intensities of BEDTTTF as a reference sample, measured by X-ray microanalyzer.

As specified above, according to this invention, there is provided a novel organic compound having excellent electron containing nature, being capable of forming a complex with an electron acceptor and being excellent in thermal stability.

Further, there is also provided an electrically conductive complex containing this novel organic compound as an electron donor.

What is claimed is:

1. An electrically conductive complex which comprises (a) a thia- and/or selenafulvalenyl group-containing compound as an electron donor and (b) an electron acceptor, the complex having an electron donor/electron acceptor molar ratio of 1/0.1 to 1/10, said thia- and/or selenafulvalenyl group-containing compound having the formula (I)

TABLE 2

| Example No. for preparation of complex | Example No. for preparation of electron donor | Electron donor (D) | Electron acceptor (A) | Elemental analysis of electron donor (wt %) | | | D/A | Electrical conductivity (S/cm) |
|---|---|---|---|---|---|---|---|---|
| | | | | I | Cl | Br | | |
| 22 | 1 | Compound (Ia) | $I_3$ | 35.4 | | | 1.3 | 20 |
| 22 | 2 | Compound (Ib) | $I_3$ | 38.1 | | | 1.1 | 50 |
| 22 | 3 | Compound (Ic) | $I_3$ | 27.0 | | | 1.1 | 200 |
| 22 | 4 | Compound (Id) | $I_3$ | 20.4 | | | 1.5 | 30 |
| 22 | 5 | Compound (Ie) | $I_3$ | 26.8 | | | 1.4 | 10 |
| 22 | 6 | Compound (If) | $I_3$ | 24.2 | | | 1.6 | 5 |
| 22 | 7 | Compound (Ig) | $I_3$ | 36.0 | | | 1.2 | 0.5 |
| 22 | 8 | Compound (Ih) | $I_3$ | 34.0 | | | 1.3 | 0.8 |
| 22 | 9 | Compound (Ii) | $I_3$ | 33.9 | | | 1.2 | 20 |
| 22 | 10 | Compound (Ij) | $I_3$ | 29.9 | | | 1.4 | 1.5 |
| 22 | 11 | Compound (Ik) | $I_3$ | 32.7 | | | 1.2 | 3 |
| 22 | 12 | Compound (Il) | $I_3$ | 28.1 | | | 1.3 | 40 |
| 22 | 13 | Compound (Im) | $I_3$ | 36.8 | | | 1.1 | 20 |
| 22 | 14 | Compound (In) | $I_3$ | 38.7 | | | 1.0 | 50 |
| 22 | 15 | Compound (Io) | $I_3$ | 31.2 | | | 1.4 | 0.2 |
| 22 | 16 | Compound (Ip) | $I_3$ | 38.7 | | | 1.1 | 60 |
| 22 | 17 | Compound (Iq) | $I_3$ | 34.1 | | | 1.3 | 20 |
| 22 | 18 | Compound (Ir) | $I_3$ | 31.6 | | | 1.1 | 200 |
| 22 | 19 | Compound (Is) | $I_3$ | 33.7 | | | 1.0 | 180 |
| 22 | 20 | Compound (It) | $I_3$ | 27.0 | | | 1.05 | 200 |
| 22 | 21 | Compound (Iu) | $I_3$ | 34.6 | | | 1.1 | 80 |
| 23 | 2 | Compound (Ib) | I | 8.0 | | | 2.6* | 0.02 |
| 24 | 1 | Compound (Ia) | $Cl_3$ | | 14.3 | | 1.2 | 1.2 |
| 25 | 2 | Compound (Ib) | $Br_3$ | | | 24.7 | 1.3 | 0.2 |
| 26 | 5 | Compound (Ie) | $I_2Br$ | 20.7 | | 6.5 | 1.2 | 10 |
| Comparative Example 2 | — | BEDTTTF | | no complex formed by direct complex-forming method | | | | |
| | — | TMTTF | | | | | | |
| Comparative Example 3 | — | TTF | I | 30.4 | | | 1.4* | 50 |

*Calculated by taking anion as I.

In crystals having a relatively large size, D/A was determined by measuring the amounts of sulfur (S) and iodine (I) with an X-ray microanalyzer. The data ob-

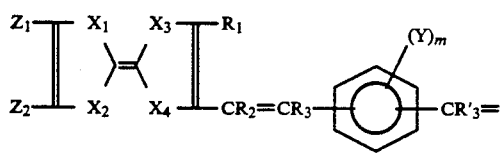
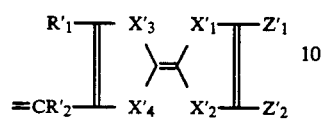

wherein:
each of $X_1$, $X_2$, $X_3$, $X_4$, $X'_1$, $X'_2$, $X'_3$ and $X'_4$ is independently S or Se,
Y is selected from the group consisting of a lower alkyl group having 1 to 5 carbon atoms, a lower alkoxy group having 1 to 5 carbon atoms, a thio lower alkyl group having 1 to 5 carbon atoms, an amino group, a hydroxyl group, a halogen atom, a cyano group and a nitro group, said Y having a size which is not so large as to prevent molecular overlapping,
m is an integer of 0 to 4,
each of $Z_1$, $Z_2$, $Z'_1$, and $Z'_2$ is independently a hydrogen atom, $C_nH_{2n+1}$ in which n is an integer of 1 to 5, or $XC_nH_{2n+1}$ in which X is S or Se and n is an integer of 1 to 5, or a combination of $Z_1$ and $Z_2$ or a combination of $Z'_1$ with $Z'_2$ are $C_nH_{2n}$ in which n is an integer of 1 to 5, or $X(C_nH_{2n})_{n'}X$ in which X is S or Se and n' is an integer of 1 to 3, and
each of $R_1$, $R_2$, $R_3$, $R'_1$, $R'_2$ and $R'_3$ is independently a hydrogen atom or $C_nH_{2n+1}$ in which n is an integer of 1 to 5,
wherein said electron acceptor (b) is an organic electron acceptor selected from the group consisting of:
7,7,8,8-tetracyanoquinodimethane, 2-methyl-7,7,8,8-tetracyanoquinodimethane, 2,5-dimethyl-7,7,8,8-tetracyanoquinodimethane, 2,5-diethyl-7,7,8,8-tetracyanoquinodimethane, 2-methoxy-7,7,8,8-tetracyanoquinodimethane, 2,5-dimethoxy-7,7,8,8-tetracyanoquinodimethane, 2-methoxy-5-ethoxy-7,7,8,8-tetracyanoquinodimethane, 2-methoxydihydrodioxabenzo-7,7,8,8-tetracyanoquinodimethane, 2-chloro-7,7,8,8-tetracyanoquinodimethane, 2-bromo-7,7,8,8-tetracyanoquinodimethane, 2,5-dibromo-7,7,8,8-tetracyanoquinodimethane, 2,5-diiodo-7,7,8,8-tetracyanoquinodimethane, 2-chloro-5-methyl-7,7,8,8-tetracyanoquinodimethane, 2-bromo-5-methyl-7,7,8,8-tetracyanoquinodimethane, 2-iodo-5-methyl-7,7,8,8-tetracyanoquinodimethane, 11,11,12,12-tetracyano-2,6-naphthoquinodimethane, 1,1,2,3,4,4-hexacyanobutadiene, sodium-13,13,14,14-tetracyanodiphenoxydimethane, tetracyanoethylene, o-benzoquinone, p-benzoquinone, 2,6-naphthoquinone, diphenoquinone, tetracyanodiquinone, p-fluoranil and tetrachlorodiphenoquinone or,
an inorganic electron acceptor selected from the group consisting of halogen atoms, trihalide anions, $SCN^-$, $Cu(NCS)_2$, $AuI_2$, $AuBr_2$, $AuCl_2$, $ClO_4$, $PF_6$ and $BF_4$.

2. The electrically conductive complex according to claim 1, wherein a group of the formula (II)

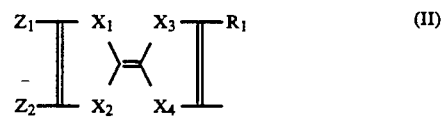

which is at one end of the formula (I) is one member selected from group consisting of

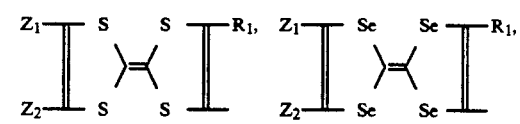

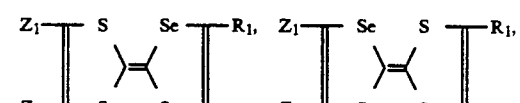

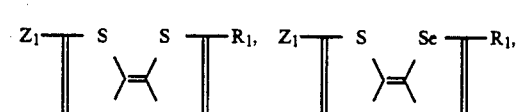

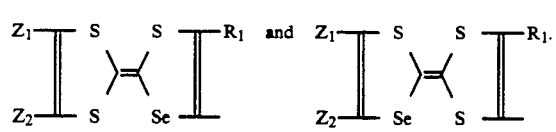

3. The electrically conductive complex according to claim 1, wherein a group of the formula (III)

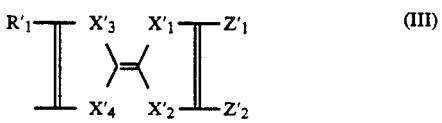

which is at one end of the formula (I) is one member selected from the group consisting of

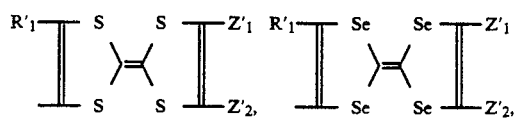

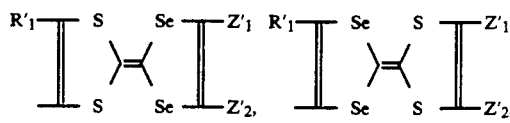

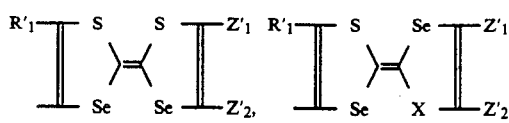

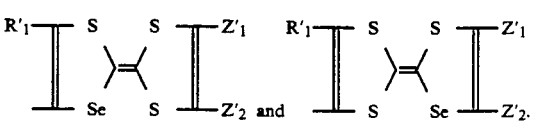

4. The electrically conductive complex according to claim 1, wherein each of $Z_1$, $Z_2$, $Z'_1$ and $Z'_2$ is independently a lower alkyl group of $C_nH_{2n+1}$ in which n is an integer of 1 to 5, and is selected from the group consisting of methyl, ethyl, n-propyl, iso-propyl, n-butyl and tert-butyl groups.

5. The electrically conductive complex according to claim 1, wherein each of $Z_1$, $Z_2$, $Z'_1$ and $Z'_2$ is independently a thio or seleno lower alkoxy group of $XC_nH_{2n+1}$ in which X is S or Se and n is an integer of 1 to 5, and is selected from the group consisting of thiomethoxy, selenomethoxy, thioethoxy, selenoethoxy, thio-n-propoxy, seleno-n-propoxy, thio-isopropoxy, seleno-iso-propoxy, thio-n-butoxy, seleno-n-butoxy, thio-iso-butoxy, seleno-iso-butoxy, thio-tert-butoxy, and seleno-tert-butoxy group.

6. The electrically conductive complex according to claim 1, wherein $Z_1$ and $Z_2$ are combined or $Z'_1$ and $Z'_2$ are combined and are a lower alkylene group of $C_nH_{2n}$, in which n is an integer of 1 to 5, which is selected from the group consisting of methylene, ethylene, propylene and butylene groups.

7. The electrically conductive complex according to claim 1, wherein $Z_1$ and $Z_2$ are combined or $Z'_1$ and $Z'_2$ are combined and each are a terminal sulfur or selenium atom-containing alkylene group of $X(CH_2)_{n'}X$ in which X is S or Se and n' is an integer of 1 to 3, which is selected from the group consisting of S—$CH_2$—S, Se—$CH_2$—Se, S—$(CH_2)_2$—S and Se—$(CH_2)_2$—Se.

8. The electrically conductive complex according to claim 1, wherein each of $R_1$, $R_2$, $R_3$, $R'_1$, $R'_2$ and $R'_3$ is a lower alkyl group of $C_nH_{2n+1}$ in which n is an integer of 1 to 5 and is selected from the group consisting of methyl, ethyl, n-propyl, iso-propyl, n-butyl, iso-butyl and tert-butyl groups.

9. The electrically conductive complex according to claim 1, wherein said electron acceptor is a halogen atom selected from the group consisting of iodine, bromine and chlorine.

10. The electrically conductive complex according to claim 11, wherein said electron acceptor is a trihalide anion selected from the group consisting of $I_3$, $I_2Br$, $Br_3$ and $Cl_3$.

11. The electrically conductive complex according to claim 1, wherein the compound of the formula (I) is selected from the group consisting of
1,4-bis[2-(tetrathiafulvalen-2-yl)vinyl]benzene,
1,4-bis[2-(tetrathiafulvalen-2-yl)vinyl]-2,5-dimethylbenzene,
1,4-bis[2-(tetraselenafulvalen-2yl)vinyl]-2,5-dimethylbenzene,
1,4-bis[2-(3,6,7-trimethyltetraselenafulvalen-2-yl)vinyl]benzene,
1,4-bis[2-(6,7-ethylenedithiotetrathiafulvalen-2-yl)vinyl]-2,5-dimethylbenzene,
1,4-bis[2-(6,7-dimethylthiotetrathiafulvalen-2-yl)vinyl]-2,5-dimethylbenzene,
1,4-bis[2-(tetrathiafulvalen-2-yl)vinyl]-2-methoxybenzene,
1,4-bis[2-(tetrathiafulvalen-2-yl)vinyl]-2-chlorobenzene,
1,4-bis[2-(3,6,7-trimethyltetrathiafulvalen-2-yl)vinyl]benzene,
1,-[2-(tetrathiafulvalen-2-yl)vinyl]-4-[2-(6,7-methylenedithiotetrathiafulvalen-2-yl)vinyl]-2,5-dimethylbenzene,
1-[2-(tetrathiafulvalen-2-yl)vinyl]-4-(2-(6,7-ethylenedithiotetrathiafulvalen-2-yl)vinyl]-2,5-dimethylbenzene,
1-[2-(tetrathiafulvalen-2-yl)vinyl]-4-[2-(tetraselenafulvalen-2-yl)vinyl]-2,5-dimethylbenzene,
1,4-bis[2-(tetrathiafulvalen-2-yl)vinyl]-2,5-dimethoxybenzene,
1,4-bis[2-(tetrathiafulvalen-2-yl)vinyl]-2,5-dichlorobenzene,
1,4-bis[2-(tetrathiafulvalen-2-yl)vinyl]-2,3,5,6-tetramethylbenzene,
1,4-bis[2-(tetrathiafulvalen-2-yl)vinyl]-2-methylbenzene,
1,4-bis[2-(tetrathiafulvalen-2-yl)vinyl]-2,5-dihydroxybenzene,
1,4-bis[2-(1,4-dithia-5,8-diselenafulvalen-2-yl)vinyl]-2,5-dimethylbenzene,
1,4-bis[2-(1,4-diselena-5,8-dithiafulvalen-2-yl)vinyl]-2,5-dimethylbenzene,
1,4-bis[2-(tetraselenafulvalen-2-yl)vinyl]-2,5-dichlorobenzene and
1,4-bis[2-(4,5,8-trithia-1-selenafulvalen-2-yl)vinyl]-2,5-dimethylbenzene.

12. The electrically conductive complex according to claim 1, wherein the electron acceptor is selected from the group consisting of iodine atom, bromine atom, chlorine atom, $I_3$ anion, $I_2Br$ anion, $Br_3$ anion, $Cl_3$ anion, $AuI_2$, $AuBr_2$, $AuCl_2$, $ClO_4$, $PF_6$, $BF_4$, 7,7,8,8,-tetracyanoquinodimethane, 2-methyl-7,7,8,8-tetracyanoquinodimethane, 2,5-dimethyl-7,7,8,8-tetracyanoquinodimethane, 2,5-diethyl-7,7,8,8-tetracyanoquinodimethane, 2-methoxy-7,7,8,8-tetracyanoquinodimethane, 2,5-dimethoxy-7,7,8,8-tetracyanoquinodimethane, 2-methoxy-5-ethoxy-7,7,8,8-tetracyanoquinodimethane, 2-methoxydihydrodioxabenzo-7,7,8,8-tetracyanoquinodimethane, 2-chloro-7,7,8,8-tetracyanoquinodimethane, 2-bromo-7,7,8,8-tetracyanoquinodimethane, 2,5-dibromo-7,7,8,8-tetracyanoquinodimethane, 2,5-diiodo-7,7,8,8-tetracyanoquinodimethane, 2-chloro-5-methyl-7,7,8,8-tetracyanoquinodimethane, 2-bromo-5-methyl-7,7,8,8-tetracyanoquinodimethane, 2-iodo-5-methyl-7,7,8,8-tetracyanoquinodimethane, 11,11,12,12-tetracyano-2,6-naphthoquinodimethane, 1,1,2,3,4,4-hexacyanobutadiene, sodium-13,13,14,14-tetracyanodiphenoxydimethane, tetracyanoethylene, o-benzoquinone, p-benzoquinone, 2,6-naphthoquinone, diphenoquinone, tetracyanodiquinone, p-fluoranil and tetrachlorodiphenoquinone; and the compound of formula (I) is selected from the group consisting of
1,4-bis[2-(tetrathiafulvalen-2-yl)vinyl]benzene,
1,4-bis[2-(tetrathiafulvalen-2-yl)vinyl]-2,5-dimethylbenzene,
1,4-bis[2-(tetraselenafulvalen-2-yl)vinyl]-2,5-dimethylbenzene,
1,4-bis[2-(3,6,7-trimethyltetraselenafulvalen-2-yl)vinyl]benzene,
1,4-bis[2-(6,7-ethylenedithiotetrathiafulvalen-2-yl)vinyl]-2,5-dimethylbenzene,
1,4-bis[2-(6,7-dimethylthiotetrathiafulvalen-2-yl)vinyl]-2,5-dimethylbenzene,
1,4-bis[2-(tetrathiafulvalen-2-yl)vinyl]-2-methoxybenzene,
1,4-bis[2-(tetrathiafulvalen-2-yl)vinyl]-2-chlorobenzene,
1,4-bis[2-(3,6,7-trimethyltetrathiafulvalen-2-yl)vinyl]benzene,
1-[2-(tetrathiafulvalen-2-yl)vinyl]-4-[2-(6,7-methylenedithiotetrathiafulvalen-2-yl)vinyl]-2,5-dimethylbenzene,
1-[2-(tetrathiafulvalen-2-yl)vinyl]-4-(2-(6,7-ethylenedithiotetrathiafulvalen-2yl)vinyl]-2,5-dimethylbenzene,
1-[2-(tetrathiafulvalen-2-yl)vinyl]-4-[2-(tetraselenafulvalen-2-yl)vinyl]-2,5-dimethylbenzene,
1,4-bis[2-(tetrathiafulvalen-2-yl)vinyl]-2,5-dimethoxybenzene, 1,4-bis[2-(tetrathiafulvalen-2-yl)vinyl]-2,5-dichlorobenzene,
1,4-bis[2-(tetrathiafulvalen-2-yl)vinyl]-2,3,5,6-tetramethylbenzene,
1,4-bis[2-(tetrathiafulvalen-2-yl)vinyl]-2-methylbenzene,
1,4-bis[2-(tetrathiafulvalen-2-yl)vinyl]-2,5-dihydroxybenzene,
1,4-bis[2-(1,4-dithia-5,8-diselenafulvalen-2-yl)vinyl]-2,5-dimethylbenzene,
1,4-bis[2-(1,4-diselena-5,8-dithiafulvalen-2-yl)vinyl]-2,5-dimethylbenzene,
1,4-bis[2-(tetraselenafulvalen-2-yl)vinyl]-2,5-dichlorobenzene and
1,4-bis[2-(4,5,8-trithia-1-selenafulvalen-2-yl)vinyl]-2,5-dimethylbenzene.

* * * * *